(12) United States Patent
Lawrence et al.

(10) Patent No.: US 11,390,663 B2
(45) Date of Patent: Jul. 19, 2022

(54) METABOLICALLY OPTIMIZED CELL CULTURE

(71) Applicant: REGENERON PHARMACEUTICALS, INC., Tarrytown, NY (US)

(72) Inventors: Shawn Lawrence, Valley Cottage, NY (US); Michelle LaFond, Pleasantville, NY (US); Ann Kim, White Plains, NY (US); Amy S. Johnson, Briarcliff Manor, NY (US); Brandon Veres, White Plains, NY (US); Mark Czeterko, Stamford, CT (US); Kristen Whalen, Brookhaven, GA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 130 days.

(21) Appl. No.: 15/130,611

(22) Filed: Apr. 15, 2016

(65) Prior Publication Data
US 2016/0230204 A1  Aug. 11, 2016

Related U.S. Application Data

(63) Continuation-in-part of application No. 15/028,521, filed as application No. PCT/US2014/005993 on Oct. 10, 2014, now abandoned.

(60) Provisional application No. 61/889,815, filed on Oct. 11, 2013.

(51) Int. Cl.
| C12P 21/06 | (2006.01) |
| C12N 5/02 | (2006.01) |
| C12N 15/63 | (2006.01) |
| C07H 21/04 | (2006.01) |
| C07K 16/00 | (2006.01) |
| C12Q 3/00 | (2006.01) |
| C12P 21/02 | (2006.01) |
| C12N 5/00 | (2006.01) |

(52) U.S. Cl.
CPC .............. *C07K 16/00* (2013.01); *C12P 21/02* (2013.01); *C12Q 3/00* (2013.01); *C07H 21/04* (2013.01); *C07K 2317/14* (2013.01); *C12N 5/0006* (2013.01); *C12N 15/63* (2013.01); *C12N 2510/00* (2013.01)

(58) Field of Classification Search
CPC .... C07K 2317/04; C12N 5/0682; C12N 5/06; C12N 2510/00; C12N 15/63; C12P 21/02; C07H 21/04
See application file for complete search history.

(56) References Cited

U.S. PATENT DOCUMENTS

| 5,045,468 A | 9/1991 | Darfler |
| 6,165,741 A | 12/2000 | Wilson et al. |
| 7,390,660 B2 | 6/2008 | Behrendt et al. |
| 7,575,890 B2 | 8/2009 | Wilson |
| 8,076,139 B1 | 12/2011 | Hamm et al. |
| 8,192,951 B2 | 6/2012 | Wang et al. |
| 8,470,552 B2 | 6/2013 | Croughan et al. |
| 2003/0087372 A1 | 5/2003 | DelaCruz et al. |
| 2003/0113915 A1* | 6/2003 | Heidemann ............ C12M 33/00 435/383 |
| 2006/0121568 A1* | 6/2006 | Drapeau ................ C07K 16/18 435/69.1 |
| 2006/0160180 A1 | 7/2006 | Drapeau et al. |
| 2008/0227136 A1 | 9/2008 | Pla et al. |
| 2011/0086411 A1 | 4/2011 | Grillberger et al. |
| 2011/0104734 A1 | 5/2011 | Croughan et al. |
| 2011/0137012 A1 | 6/2011 | Katayama et al. |

FOREIGN PATENT DOCUMENTS

| CN | 101300342 A | 11/2008 |
| DZ | 2783 A1 | 8/2005 |
| EP | 1 268 748 B1 | 1/2008 |
| EP | 3 351 620 A1 | 7/2018 |
| JP | 2008-511330 A | 4/2008 |
| JP | 2011-524172 A | 9/2011 |
| JP | 2013-524825 A | 6/2013 |
| WO | WO 2004/104186 A1 | 12/2004 |
| WO | 2009/023562 A2 | 2/2009 |
| WO | 2013/006479 A2 | 1/2013 |
| WO | 2014/073967 A1 | 5/2014 |

(Continued)

OTHER PUBLICATIONS

Templeton et al., "Peak Antibody Production is Associated With Increased Oxidative Metabolism in an Industrially Relevant Fed-Batch CHO Cell Culture", Biotechnology and Bioengineering, published online Mar. 4, 2013, vol. 110, No. 7, pp. 2013-2024.*
Mulukutla B C et al., "On Metabolic Shift to Lactate Consumption in Fed-Batch Culture of Mammalian Cells", Metabolic Engineering 14(2):138-149 (2012).
Zhou W. et al., "Fed-Batch Culture of Recombinant NS0 Myeloma Cells With High Monoclonal Antibody Production", Biotechnology and Bioengineering 55(5):783-792 (Sep. 5, 1997).
Young J D et al., "Metabolic Flux Rewiring in Mammalian Cell Cultures", Current Opinion in Biotechnology 24:1108-1115 (2013).
Extended Supplementary European Search Report dated Aug. 29, 2016 received in European Patent Application No. 14 85 1841.8.
Bleckwenn NA et al., "Large-Scale Cell Culture", Curr Protoc Immunol. 59:Appendix 1, (44 pages) (May 2004).
Cruz HJ et al., "Metabolic Shifts by Nutrient Manipulation in Continuous Cultures of BHK Cells", Biotechnol Bioeng. 66(2):104-113 (1999).

(Continued)

*Primary Examiner* — Shin Lin Chen
(74) *Attorney, Agent, or Firm* — Scully, Scott, Murphy & Presser, P.C.; Todd R. Samelman

(57) ABSTRACT

Improved methods for large scale production of proteins and/or polypeptides in cell culture is provided. In accordance with the present invention, the method provides for culturing cells that have metabolically shifted. The use of such a method or system allows high levels of protein or polypeptide production and reduces accumulation of unwanted metabolic waste such as lactate. Proteins and polypeptides expressed in accordance with the present invention may be advantageously used in the preparation of pharmaceutical, immunogenic, or other commercial biologic compositions, such as antibodies.

15 Claims, 13 Drawing Sheets

(56) References Cited

FOREIGN PATENT DOCUMENTS

WO 2015/054554 A1 4/2015

OTHER PUBLICATIONS

Dela Luz-Hdez K., "Metabolomics and Mammalian Cell Culture", Metabolomics, Dr Ute Roessner (Ed.), ISBN 978-953-51-0046-1, InTech, Available from: http:www.intechopen.com/books/metabolomics/metabolomics-and-mammalian-cell-cultures, (17 pages) (2012).
Dezengotita V.M. et al., "Effects of CO2 and Osmolality on Hybridoma Cells: Growth, Metabolism and Monoclonal Antibody Production", Cytotechnology 28:213-227 (1998).
Europa AF et al., "Multiple Steady States With Distinct Cellular Metabolism in Continuous Culture of Mammalian Cells", Biotechnol Bioeng. 67(1):25-34 (Jan. 2000).
Gambhir A. et al., "Analysis of Cellular Metabolism of Hybridoma Cells at Distinct Physiological States", J. Biosci Bioeng. 95(4):317-327 (2003).
Goudar C.T. et al., "Decreased pCO2 Accumulation by Eliminating Bicarbonate Addition to High Cell-Density Cultures", Biotechnology and Bioengineering 96(6):1107-1117 (Apr. 15, 2007).
Hotter G. et al., "Low O2 and High CO2 in LLC-PK1 Cells Culture Mimics Renal Ischemia-Induced Apoptosis", Laboratory Investigation 84:213-220 (2004).
Kim B.J. et al., "Batch, Fed-Batch, and Microcarrier Cultures With CHO Cell Lines in a Pressure-Cycle Driven Miniaturized Bioreactor", Biotechnology and Bioengineering109(1):137-145 (Jan. 2012).
Kim S.H. et al., "Down-Regulation of Lactate Dehydrogenase-A by siRNAs for Reduced Lactic Acid Formation of Chinese Hamster Ovary Cells Producing Thrombopoietin", Appl Microbiol Biotechnol. 74(1):152-159 (Feb. 2007).
Kim S.H. et al., "Functional Expression of Human Pyruvate Carboxylase for Reduced Lactic Acid Formation of Chinese Hamster Ovary Cells (DG44)", Appl Microbiol Biotechnol. 76(3):659-665 (Sep. 2007).
Kimura R. et al., "Effects of Elevated pCO2 and/or Osmolality on the Growth and Recombinant tPA Production of CHO Cells", Biotechnology and Bioengineering 52(1):152-160 (Oct. 5, 1996).
Le H. et al., "Multivariate Analysis of Cell Culture Bioprocess Data-Lactate Consumption as Process Indicator", Journal of Biotechnology 162:210-223 (2012).
Li F. et al., "Cell Culture Processes for Monoclonal Antibody Production", mABS 2(5):466-479 (Sep./Oct. 2010).
Ma N. et al., "A Single Nutrient Feed Supports Both Chemically Defined NS0 and CHO Fed-Batch Processes: Improved Productivity and Lactate Metabolism", Biotechnol Prog. 25(5):1353-1363 (2009).
Mostafa S.S. et al., "Strategies for Improved dCO2 Removal in Large-Scale Fed-Batch Cultures", Biotechnol. Prog. 19(1):45-51 (2003).
Newland M. et al., "Ammonia Inhibition of Hybridomas Propagated in Batch, Fed-Batch, and Continuous Culture", Biotechnol Bioeng. 43(5):434-438 (Mar. 1994).
Omasa T. et al., "Cell Engineering and Cultivation of Chinese Hamster Ovary (CHO) Cells", Curr Pharm Biotechnol. 11(3):233-240 (Apr. 2010).
Ozturk S.S. et al., "Effects of Ammonia and Lactate on Hybridoma Growth, Metabolism, and Antibody Production", Biotechnology and Bioengineering 39:418-431 (1992).
Pattison R.N. et al., "Measurement and Control of Dissolved Carbon Dioxide in Mammalian Cell Culture Processes Using an in Situ Fiber Optic Chemical Sensor", Biotechnol. Prog. 16(5):769-774 (2000).
Quek L.E. et al., "Metabolic Flux Analysis in Mammalian Cell Culture", Metab Eng. 12(2):161-171 (Mar. 2010).
Sheikholeslami Z. et al., "The Impact of the Timing of Induction on the Metabolism and Productivity of CHO Cells in Culture", Biochemical Engineering Journal 79:162-171 (2013).
Wlaschin K.F. et al., "Engineering Cell Metabolism for High-Density Cell Culture Via Manipulation of Sugar Transport", J. Biotechnol. 131(2):168-176 (Aug. 2007).
Xie L. et al., "Fed-Batch Cultivation of Animal Cells Using Different Medium Design Concepts and Feeding Strategies", Biotechnol. Bioeng. 43(11):1175-1189 (May 1994).
Zagari F. et al., "Lactate Metabolism Shift in CHO Cell Culture: The Role of Mitochondrial Oxidative Activity", N. Biotechnol. 30(2):238-245 (Jan. 2013).
Zhou W. et al., "Alteration of Mammalian Cell Metabolism by Dynamic Nutrient Feeding", Cytotechnology 24:99-108 (1997).
International Search Report and Written Opinion dated Jan. 14, 2015 received in International Application No. PCT/US2014/059993.
Japanese Notice of Reasons for Rejection dated Aug. 3, 2018 received in Japanese Patent Application No. 2016-547976, together with an English-language translation.
Sun X. et al., "Effects of Lactate on Growth, Metabolism and EPO Expression of Recombinant CHO Cells", Journal of Chemical Industry and Engineering 53(10):1034-1039 (Oct. 2002), together with an English-language abstract.
Xiaoshu W. et al., "CD147/HAb18G Monoclonal Antibody Suppresses Glycolysis Lactic Acid Metabolism in Human Glioma Cells In Vitro", Acta Academiae Medicinae Militaris Tertiae 32(20):2193-2196 (Oct. 30, 2010), together with an English-language abstract.
Chinese Office Action dated Jun. 11, 2018 received in Chinese Patent Application No. 201480055499.4, together with an English-language translation.
Li J. et al., "Feeding Lactate for CHO Cell Culture Processes: Impact on Culture Metabolism and Performance", Biotechnology and Bioengineering 109(5):1173-1186 (May 2012).
Luo J. et al., "Comparative Metabolite Analysis to Understand Lactate Metabolism Shift in Chinese Hamster Ovary Cell Culture Process", Biotechnology and Bioengineering 109(1):146-156 (Jan. 2012).
Notice of European Opposition to European Patent No. 3055409 dated Feb. 4, 2019.
Communication from the European Patent Office dated Sep. 23, 2019 received in European Patent No. 3055409, enclosing submission of Opponent.
Cong C. et al., "A Novel Scale-Up Method for Mammalian Cell Culture in Packed-Bed Bioreactor", Biotechnology Letters 23:881-885 (2001).
Goudar C.T. et al., "Logistic Equations Effectively Model Mammalian Cell Batch and Fed-Batch Kinetics by Logically Constraining the Fit", Biotechnology Progress 21(4):1109-1118 (2005).
Kumar N. et al., "Exploring Packaged Microvesicle Proteome Composition of Chinese Hamster Ovary Secretome", Journal of Bioprocessing & Biotechniques 6(4):1000274 (2016).
Meuwly F. et al., "Conversion of a CHO Cell Culture Process from Perfusion to Fed-Batch Technology Without Altering Product Quality", Journal of Biotechnology 123:106-116 (2006).
Pohlscheidt M. et al., "Optimizing Capacity Utilization by Large Scale 3000 L Perfusion in Seed Train Bioreactors", Biotechnol. Prog. 29(1):222-229 (2013).
Sauer P.W. et al., "A High-Yielding, Generic Fed-Batch Cell Culture Process for Production of Recombinant Antibodies", Biotechnology and Bioengineering 67(5):585-597 (Mar. 5, 2000).
Smelko J P et al., "Performance of High Intensity Fed-Batch Mammalian Cell Cultures in Disposable Bioreactor Systems", Biotechnol. Prog. 27(5):1358-1364 (2011).
"Guidelines to Maintain Cultured Cells", ThermoFisher Scientific (2016) (total 4 pages).
Bibila T. et al., "A Structured Model for Monoclonal Antibody Synthesis in Exponentially Growing and Stationary Phase Hybridoma Cells", Biotechnology and Bioengineering 37:210-226 (Feb. 1991).
International Application No. PCT/NL/2013/050805 dated Nov. 8, 2013.
International Preliminary Report on Patentability dated Feb. 18, 2015 received in International Application No. PCT/NL/2013/050805.
Submission by Opponent dated Apr. 20, 2021 in EP Patent 3055409 B1.

(56) References Cited

OTHER PUBLICATIONS

EPO Communication dated Apr. 28, 2021 in EP Patent 3055409 B1, forwarding Submission by Opponent dated Apr. 20, 2021.
Written Decision dated Oct. 4, 2021 from the Opposition Division of the European Patent Office regarding EP 3 055 409 B1.
Abu-Absi S. et al., "Cell Culture Process Operations for Recombinant Protein Production", Adv Biochem Eng Biotechnol 139:35-68 (2014).
Birch J.R. et al., "Antibody Production", Advanced Drug Delivery Reviews 58:671-685 (2006).
Tsao Y-S et al., "Monitoring Chinese Hamster Ovary Cell Culture by the Analysis of Glucose and Lactate Metabolism", Journal of Biotechnology 118:316-327 (2005).
EPO Communication dated Jun. 16, 2021 received in European Application No. 18161278.9 (EP Patent 3 351 620), forwarding a Notice of Opposition filed by Maiwald and a Notice of Opposition filed by Breuer.

\* cited by examiner

METABOLICALLY OPTIMIZED CELL CULTURE

CROSS-REFERENCE TO RELATED APPLICATIONS

The present application is a continuation in-part of U.S. patent application Ser. No. 15/028,521, filed on Apr. 11, 2016, which is the national phase of PCT/US2014/059993, filed on Oct. 10, 2014, which claims the benefit of U.S. Provisional Patent Application No. 61/889,815, filed Oct. 11, 2013, the entire contents of all of which are specifically incorporated by reference in their entirety.

FIELD OF THE INVENTION

The present invention relates to cells that metabolically shift to lactate consumption in cell culture and cell culture methods of producing the same. A switch to a lactate consumption metabolic profile in seed train culture has beneficial effects on production culture, such as increased protein titer and improved cell health and growth. When cells are cultured to certain viable cell concentrations prior to inoculation of a production reactor, cells exhibit an improved protein titer due to, for example, more efficient lactate metabolism, low lactate production rate, low peak lactate levels. Thus, an improved method for large scale production of proteins and/or polypeptides in cell culture is provided.

BACKGROUND OF THE INVENTION

Biological agents, particularly proteins and polypeptides, are being developed more often as novel pharmaceutical products. Engineered cells that produce unusually high levels of the particular protein of interest have become critically important for successful commercial production of these pharmaceutical interventions. Control and optimization of cell culture conditions varies and has great effect on the level and quality of the therapeutic protein produced in culture.

It is customary to manufacture proteins via cell culture in a batch or fed-batch process. Early stages of inoculum growth after vial thaw include culturing cells in a seed culture. Typically, cells are grown at an exponential growth rate, such as in seed train bioreactors, in order to progressively increase size and/or volume of the cell population. After cell mass is scaled up through several cell culture bioreactor stages, cells are then transferred to a production bioreactor while the cells are still in exponential growth (log phase). See Gambhir, A. et al., 2003, *J Bioscience Bioeng* 95(4):317-327. It is generally considered undesirable to allow cells in batch culture, for example seed culture, to go past the log phase into stationary phase. Therefore, it has been recommended that cultures should be passaged while they are in log phase, before, cells, e.g. adherent cells, reach confluence due to contact inhibition or accumulation of waste products inhibits cell growth, among other reasons. See *Cell Culture Basics*, Gibco/Invitrogen Online Handbook, www.invitrogen.com; and ATCC® Animal Cell Culture Guide, www.atcc.org.

Following transfer to fed-batch culture, cells are cultured for a period of time during which the composition of the medium is monitored and controlled to allow production of the protein or polypeptide of interest. After a particular yield is reached or cell viability, waste accumulation or nutrient depletion determines that the culture should be terminated and the produced protein or polypeptide must be isolated. Many significant advances have been made over the past decade intending to improve recombinant protein yield, which currently reaches titers of multiple grams per liter. Advancements in protein manufacturing processes, as well as in cell line engineering, and cell culture medium and feed development, have contributed to the gain in protein yield.

Fed-batch production involves the addition of small volumes of feed to supplement the nutrients present in the bioreactor as cell growth and product production progresses. It is understood that, in general, mammalian cells tend to continuously metabolize carbohydrates resulting in lactate accumulation, thus requiring the addition of a base to the cell culture medium to neutralize the lactic acid. Base addition elevates osmolality in the cell medium, which in turn greatly restricts the overall achievable cell viability and/or productivity in the bioreactor. Accumulation of lactate in the medium is detrimental to cell growth and is one of the common factors that limit the maximum titer productivity that can be achieved in batch culture. In a typical batch cell culture, growth and productivity is inhibited after lactate concentration in the culture reaches approximately 30-50 mM and/or ammonia concentration reaches 3-5 mM. See Ozturk, S. S., Riley, M. R., and Palsson, B. O. 1992. *Biotechnol. and Bioeng.* 39: 418-431. To date, widely adopted schemes include nutrient supplementation and the design of chemically defined, serum-free media to support continuous cell growth and optimum protein secretion.

Efforts particularly related to reducing the output of metabolic waste products, such as accumulation of lactate, in cell culture have improved the overall quantity of final protein titers. To date, these efforts are focused on controlled glucose or nutrient-limited fed-batch processes (see, e.g., WO2004104186; U.S. Pat. No. 8,192,951B2), improved cell culture medium conditions (e.g., U.S. Pat. No. 7,390,660; and Zagari, et al., 2013, *New Biotechnol.*, 30(2):238-45), or cellular engineering, including targeting enzymes in the glycolysis pathway (e.g., Kim, S. H. and Lee, G. M., 2007, *Appl. Microbiol. Biotechnol.* 74, 152-159; Kim, S. H. and Lee, G. M., 2007, *Appl. Microbiol. Biotechnol.* 76, 659-665; and Wlaschin, K. F. and Hu, W-S., 2007, *J. Biotechnol.* 131, 168-176).

Controlled feeding of cells is utilized in an effort to reach a more efficient metabolic phenotype. See Europa, A. F., et al., 2000, *Biotechnol. Bioeng.* 67:25-34; Cruz et al., 1999, *Biotechnol Bioeng*, 66(2):104-113; Zhou et al., 1997, *Cytotechnology* 24, 99-108; and Xie and Wang, 1994, *Biotechnol Bioeng*, 43:1174-89. However, this optimization method is complicated by the fact that nutrient deprivation, as well as rapid changes in, for example, ammonia concentration seen at high cell density fed-batch culture can induce apoptosis ("programmed cell death"). See Newland et al., 1994, *Biotechnol. Bioeng.* 43(5):434-8. Hence, a common optimization approach is to grow cells to moderately high density in fed-batch and then deliberately induce a prolonged, productive stationary phase by, e.g., a temperature or pH change. See Quek et al., 2010, *Metab Eng* 12(2):161-71.

Optimization techniques, such as those discussed supra, have focused on fed-batch cell culture and such nutrient-dependent processes must be adapted for each host cell engineered for production of a polypeptide of interest. Therefore, methods to adapt cells to lactate consumption in seed train culture are highly desirous in the process of manufacturing biological therapeutics. Optimizing a cell line with a metabolic phenotype for lactate consumption would prove beneficial to commercial production of polypeptides.

SUMMARY OF THE INVENTION

The invention provides cells and methods of culturing cells that have metabolically-shifted to lactate consumption. Metabolically adapted cells are ideal for large scale protein production.

One aspect of the invention is a method of culturing cells comprising transferring cells from a first cell culture to a second cell culture after a metabolic shift to lactate consumption in the cells has occurred in the first culture.

In a related aspect of the invention a method of culturing cells is provided that includes culturing cells in a first cell culture, determining a metabolic shift to lactate consumption in the cells has occurred in the first cell culture, transferring an amount of cells from the first cell culture to a second cell culture after the metabolic shift to lactate consumption in the cells has occurred, then culturing cells in the second cell culture to achieve a predetermined viable cell concentration, and then transferring an amount of cells from the second cell culture to a production cell culture, wherein viable cell concentration is increased in the production cell culture. In certain embodiments, cells in the first cell culture are cultured to a viable cell concentration of greater than $3.0 \times 10^6$ cells/mL, which results in an early shift to lactate consumption. In other embodiments, a shift to lactate consumption is achieved when cells in the first cell culture are cultured to a viable cell concentration of $3.5 \times 10^6$ cells/mL to $5.0 \times 10^6$ cells/mL prior to transfer of at least a portion of the cells in the first cell culture to a second cell culture. In other embodiments, cells in the first cell culture are cultured to a viable cell concentration of $3.5 \times 10^6$ cells/mL, $4.0 \times 10^6$ cells/mL, $4.5 \times 10^6$ cells/mL or $5.0 \times 10^6$ cells/mL prior to transfer of at least a portion of the cells in the first cell culture to a second cell culture. In certain embodiments, the method further provides detecting a reduced rate of lactate accumulation in the first cell culture prior to transfer to the second cell culture compared to that determined in an otherwise identical cell culture under otherwise identical conditions except that transferring cells to the second cell culture is performed prior to a metabolic shift, or is performed prior to the viable cell count reaching $3.0 \times 10^6$ cells/mL.

In a specific embodiment, cells in the first cell culture are cultured to a viable cell concentration of greater than $3.0 \times 10^6$ cells/mL cells, which induces an early shift to lactate consumption and subsequently, a portion of the cells from the first cell culture are transferred to a second cell culture, whereby the cells in the second cell culture are cultured to a viable cell concentration of at least $3.0 \times 10^6$ cells/mL prior to transferring a portion of the cells in the second cell culture to a production culture. In certain embodiments, cells in the second cell culture are cultured to a viable cell concentration of $3.0 \times 10^6$ cells/mL to $5.0 \times 10^6$ cells/mL prior to transfer of at least a portion of the cells in the second cell culture to a production cell culture. In other embodiments, cells in the second cell culture are cultured to a viable cell concentration of $3.0 \times 10^6$ cells/mL, $3.5 \times 10^6$ cells/mL, $4.0 \times 10^6$ cells/mL, $4.5 \times 10^6$ or $5.0 \times 10^6$ cells/mL prior to transfer of at least a portion of the cells in the second cell culture to a production cell culture. In yet another embodiment cells in the second cell culture are cultured to a viable cell concentration of greater than $3.0 \times 10^6$ cells/mL prior to transfer.

In another embodiment of the invention, cells in the first cell culture are cultured to a predetermined viable cell culture concentration, then a portion of cells from the first cell culture is transferred to a second cell culture and cultured to achieve a viable cell concentration of greater than $3.0 \times 10^6$ cells/mL prior to transfer to a production cell culture, whereby a metabolic shift to lactate consumption is observed in the cells in the second cell culture prior to transfer. In certain embodiments, a shift to lactate consumption is achieved when cells in the second cell culture are cultured to a viable cell concentration of $3.5 \times 10^6$ cells/mL to $5.0 \times 10^6$ cells/mL prior to transfer of at least a portion of the cells in the second cell culture to a production cell culture. In other embodiments, cells in the second cell culture are cultured to a viable cell concentration of $3.5 \times 10^6$ cells/mL, $4.0 \times 10^6$ cells/mL, $4.5 \times 10^6$ or $5.0 \times 10^6$ cells/mL prior to transfer of at least a portion of the cells in the second cell culture to a production cell culture. In certain embodiments, the method further provides detecting a reduced rate of lactate accumulation in the second cell culture prior to transfer to the production cell culture compared to that determined in an otherwise identical cell culture under otherwise identical conditions except that transferring cells to the second cell culture is performed prior to a metabolic shift, or is performed prior to the viable cell count reaching $3.0 \times 10^6$ cells/mL.

Another aspect of the invention provides a method of culturing cells comprising culturing cells in a first cell culture, determining that a metabolic shift to lactate consumption in the cells has occurred in the first cell culture, and transferring the cells to a second cell culture after the metabolic shift to lactate consumption in the cells has occurred, wherein lactate concentration in the second cell culture indicates net lactate consumption during the second culture. In one embodiment, the method further provides a decrease in accumulation of lactate in the second cell culture compared to that determined in an otherwise identical cell culture under otherwise identical conditions except transferring cells to the second cell culture is before a metabolic shift has occurred in the first cell culture.

Yet another aspect of the invention provides a method of producing a protein comprising transferring cells from a first cell culture to a second cell culture after a metabolic shift to lactate consumption in the cells has occurred, and maintaining the second cell culture for a period of time so that the protein accumulates in the cell culture. In a related aspect, the invention provides a method of producing a protein comprising culturing cells in a first cell culture, determining a metabolic shift to lactate consumption in the cells has occurred in the first cell culture, transferring the cells to a second cell culture after the metabolic shift to lactate consumption in the cells has occurred, and maintaining the second cell culture for a period of time so that the protein accumulates in the cell culture. In one embodiment, the method further provides an increase in productivity in the second cell culture compared to that determined in an otherwise identical cell culture under otherwise identical conditions except that transferring cells to the second cell culture is performed prior to a metabolic shift, or is performed prior to the viable cell count reaching $3.0 \times 10^6$ cells/mL.

Another aspect of the invention provides an improved method of culturing cells, wherein the cells comprise a gene encoding a polypeptide of interest, comprising the steps of: culturing cells in a first cell culture, maintaining the first cell culture under conditions that allow the expansion of the cell mass, transferring the cells to a second cell culture after the metabolic shift to lactate consumption in the cells has occurred, maintaining the second cell culture under conditions that allow the expression of the polypeptide of interest, and harvesting the polypeptide of interest from the second cell culture. In one embodiment, the method further comprises determining a metabolic shift to lactate consumption in the cells has occurred in the first cell culture.

Another aspect of the invention provides an improved method of producing a polypeptide in a cell culture comprising the steps of: transfecting cells with DNA encoding a polypeptide of interest, culturing the cells in a first cell culture, transferring the cells to a second cell culture after the metabolic shift to lactate consumption in the cells has occurred, wherein the polypeptide of interest is expressed under conditions of a second cell culture, and maintaining the second cell culture for a period of time so that the polypeptide accumulates in the cell culture. In one embodiment, the method further comprises determining a metabolic shift to lactate consumption in the cells has occurred in the first cell culture.

In another of the invention a method of producing a metabolically shifted cell line is provided, comprising the steps of: maintaining a cell population in a first cell culture under conditions that allow the expansion of the cell mass, determining when a metabolic shift to lactate consumption in the cells has occurred, transferring a fraction of the cell population from the first cell culture to a second cell culture after the metabolic shift to lactate consumption in the cells has occurred, maintaining the cell population in the second cell culture for a period of time, and optionally harvesting the cells thus producing the metabolically shifted cell line.

Another aspect of the invention provides a metabolically shifted cell line produced by any of the methods of the invention disclosed herein. In some embodiments, the metabolically shifted cell comprises a nucleic acid sequence stably integrated into the cellular genome wherein the nucleic acid sequence encodes a polypeptide or protein of interest. In other embodiments, the metabolically shifted cell comprises an expression vector encoding a polypeptide or protein of interest.

In one embodiment of any of the methods provided herein, the metabolic shift to lactate consumption is detected by pH, lactate or base measurements in the first cell culture. In other embodiments, the cells are transferred to a second cell culture and lactate consumption is detected. In certain embodiments, a metabolic shift to lactate consumption is detected in the first cell culture and maintained (e.g., confirmed) in the second cell culture. In still other embodiments, the metabolic shift to lactate consumption is detected after pH increases in the first cell culture medium without addition of base. In other embodiments, the metabolic shift to lactate consumption is detected when lactate levels plateau in a cell culture. In still other embodiments, the methods further comprise determining the metabolic shift by measuring pH in a cell culture, adding base to maintain pH above a predetermined lower limit, determining that the pH is above the predetermined lower limit for consecutive intervals, and ceasing the addition of base, thereby determining that the metabolic shift to lactate consumption has occurred in the cell culture. In other embodiments, the metabolic shift to lactate consumption is detected by indicators or products of cell metabolism, including but not limited to oxygen consumption, and metabolites such as glycine, tryptophan, phenylalanine, adenine, palmitic acid, glutamic acid, methionine and asparagine. In another embodiment, the metabolic shift to lactate consumption is detected by metabolic analysis or proteomic analysis. In one embodiment, the metabolic shift occurs when the cells emerge from log (i.e., exponential growth) phase in a cell culture. In another embodiment, the metabolic shift occurs when the cells have reached stationary growth phase. In yet another embodiment, the cells are transferred after the cells have reached stationary growth phase.

In one embodiment, the metabolic shift occurs in the first cell culture on or after 3 days of cell growth in the first cell culture. In another embodiment, the metabolic shift occurs in the first cell culture on or after 3.5 days of cell growth in the first cell culture.

In some embodiments, the first cell culture and second culture are seed cultures. In some embodiments, the first and/or second cell cultures are a seed train culture. In some embodiments, the first and/or second cell cultures are a fed-batch culture. In other embodiments, the second cell culture is performed in a production bioreactor.

In some embodiments of the present methods, lactate concentration in the second cell culture indicates net lactate consumption, for example, net lactate consumption is achieved on or after 2 days, 3 days, 4 days, or 5 days of cell growth in the second cell culture. In other embodiments, the decrease in accumulation of lactate is a reduction in peak lactate concentration in the second cell culture. In other embodiments, the reduction in peak lactate concentration occurs in the second cell culture on or after 5 days of cell growth in the second cell culture. In other embodiments, peak lactate concentration in the second cell culture is less than about 6 g/L, 5 g/L, 4 g/L, 3 g/L, 2 g/L, or less than about 1 g/L.

In some embodiments of the invention, the cell or cells are selected from the group consisting of CHO, COS, retinal, Vero, CV1, HEK293, 293 EBNA, MSR 293, MDCK, HaK, BHK21, HeLa, HepG2, W138, MRC 5, Colo25, HB 8065, HL-60, Jurkat, Daudi, A431, CV-1, U937, 3T3, L cell, C127 cell, SP2/0, NS-0, MMT, PER.C6, murine lymphoid, and murine hybridoma cells.

BRIEF DESCRIPTION OF THE DRAWINGS

FIG. 5A shows that an increase in viable cell density (VCC) in a first seed train culture (N-2) and/or in a second seed train culture (N-1) bioreactor results in an increase in the maximum titer in the production culture bioreactor when compared to titer profiles resulting from cells cultured to a lower viable cell concentration in the first seed train culture (N-2: $1.5\times10^6$ cells/mL VCC). Increasing the final VCCs in both the N-2 and N-1 seed train culture steps to greater than $3.0\times10^6$ cells/mL (e.g., $4.5\times10^6$ cell/mL and $5\times10^6$ cells/mL) results in about a 1.5 fold increase in the maximum titer when compared to the maximum titer exhibited in the production culture step when the N-2 and N-1 seed train cell culture steps were each grown to a final VCC of $3.0\times10^6$ or lower. The detected lactate accumulation rate in the N-2 seed train culture step was reduced when the final VCC of the N-2 seed train culture step reached $4.5\times10^6$ cells/mL. Further, the lactate accumulation rate in the N-1 seed train culture step was reduced when the final VCC of the N-1 seed train culture step reached $5.0\times10^6$ cells/mL. FIG. 5B shows a statistical analysis for the maximum titer profiles exhibited under the following experimental conditions: from left to right, N-2: $1.5\times10^6$ cell/mL, N-1: $3.0\times10^6$ cell/mL; (N-2: $3.0\times10^6$ cell/mL, N-1: $3.0\times10^6$ cell/mL); (N-2: $4.5\times10^6$ cell/mL, N-1: $3.0\times10^6$ cell/mL); (N-2: $3.0\times10^6$ cell/mL, N-1: $5.0\times10^6$ cell/mL); and (N-2: $4.5\times10^6$ cell/mL, N-1: $5.0\times10^6$ cell/mL). Increasing the VCCs in both the N-2 and N-1 seed train culture steps to greater than $3.0\times10^6$ cells/mL (e.g., $4.5\times10^6$ cell/mL and $5\times10^6$ cells/mL) (N-2: $4.5\times10^6$ cell/mL, N-1: $5.0\times10^6$ cell/mL), resulted in statistically significantly (p 0.05) higher maximum protein titer than conditions with final viable cell concentrations of $3.0\times10^6$ cells/mL or lower (N-2: $3.0\times10^6$ cell/mL, N-1: $3.0\times10^6$ cell/mL and N-2: $1.5\times10^6$ cell/mL, N-1: $3.0\times10^6$ cell/mL). Greater maximum protein titers in the production cell culture bioreactor were achieved for any seed train culture process in which the final N-2 or N-1 viable cell concentration(s) were greater than $3.0\times10^6$ cells/mL prior to transfer, which resulted with a reduced rate of lactate accumulation when compared to final N-2 and/or N-1 viable cell concentration(s) below $3.0\times10^6$ cells/mL.

FIG. 7A shows that an increase of the viable cell concentration to greater than $3.0\times10^6$ cell/mL in a first seed train culture (N-2) and/or in a second seed train culture (N-1) bioreactor results in lower peak and final lactate concentration when compared to titer profiles resulting from a lower viable cell concentration in the first seed train culture (e.g., N-2: $1.5\times10^6$ cells/mL VCC) and when both the N-2 seed train and N-1 seed train culture were grown to a final VCC of $3.0\times10^6$ cells/mL prior to transfer. Increasing the final VCCs in both the N-2 and N-1 seed train culture steps to greater than $3.0\times10^6$ cells/mL (e.g., $4.5\times10^6$ cell/mL and $5\times10^6$ cells/mL) resulted in reduced lactate accumulation rate in both the N-1 and N-2 seed train culture steps, respectively. The reduced rate of lactate accumulation in the seed culture steps correlate to a lower peak and reduced lactate accumulation in the production culture compared to the lactate accumulation rate exhibited in the production culture when the N-2 and N-1 seed train cell culture steps were each grown to a final VCC of less than $3.0\times10^6$ cells/mL. FIG. 7B shows a statistical analysis for the peak lactate concentration and final lactate concentration exhibited for the following experimental conditions: N-2: $1.5\times10^6$ cell/mL, N-1: $3.0\times10^6$ cell/mL; N-2: $3.0\times10^6$ cell/mL, N-1: $3.0\times10^6$ cells/mL; N-2: $4.5\times10^6$ cells/mL, N-1: $3.0\times10^6$ cells/mL; N-2: $3.0\times10^6$ cells/mL, N-1: $5.0\times10^6$ cell/mL; and N-2: $4.5\times10^6$ cells/mL, N-1: $5.0\times10^6$ cells/mL. Increasing the VCCs in both the N-2 and N-1 seed train culture steps to $4.5\times10^6$ cells/mL and $5.0\times10^6$ cells/mL, respectively (N-2: $4.5\times10^6$ cells/mL, N-1: $5.0\times10^6$ cells/mL), resulted in statistically significantly (p 0.05) reductions in peak lactate concentrations when compared to other cell cultures grown to a final viable cell concentration of $3.0\times10^6$ cells/mL or lower (N-2: $1.5\times10^6$ cell/mL, N-1: $3.0\times10^6$ cell/mL and N-2: $3.0\times10^6$ cell/mL, N-1: $3.0\times10^6$ cells/mL). Reduced peak lactate concentrations were also observed in the production cell culture bioreactor for any seed train culture process in which the final N-2 and/or N-1 viable cell concentration(s) was greater than $3.0\times10^6$ cells/mL (N-2: $4.5\times10^6$ cells/mL, N-1: $3.0\times10^6$ cells/mL; N-2: $3.0\times10^6$ cells/mL, N-1: $5.0\times10^6$ cell/mL; and N-2: $4.5\times10^6$ cells/mL, N-1: $5.0\times10^6$ cells/mL), which resulted with a reduced rate of lactate accumulation when compared to final N-2 and/or N-1 viable cell concentration(s) of $3.0\times10^6$ cells/mL or lower (N-2: $1.5\times10^6$ cell/mL, N-1: $3.0\times10^6$ cell/mL and N-2: $3.0\times10^6$ cell/mL, N-1: $3.0\times10^6$ cells/mL). Reduced peak and final lactate concentrations in conditions N-2: $4.5\times10^6$ cells/mL, N-1: $3.0\times10^6$ cells/mL, N-2: $3.0\times10^6$ cells/mL, N-1: $5.0\times10^6$ cell/mL, and N-2: $4.5\times10^6$ cells/mL, N-1: $5.0\times10^6$ cells/mL were correlated with a reduced rate of lactate accumulation.

DETAILED DESCRIPTION OF THE INVENTION

Figure 1A:
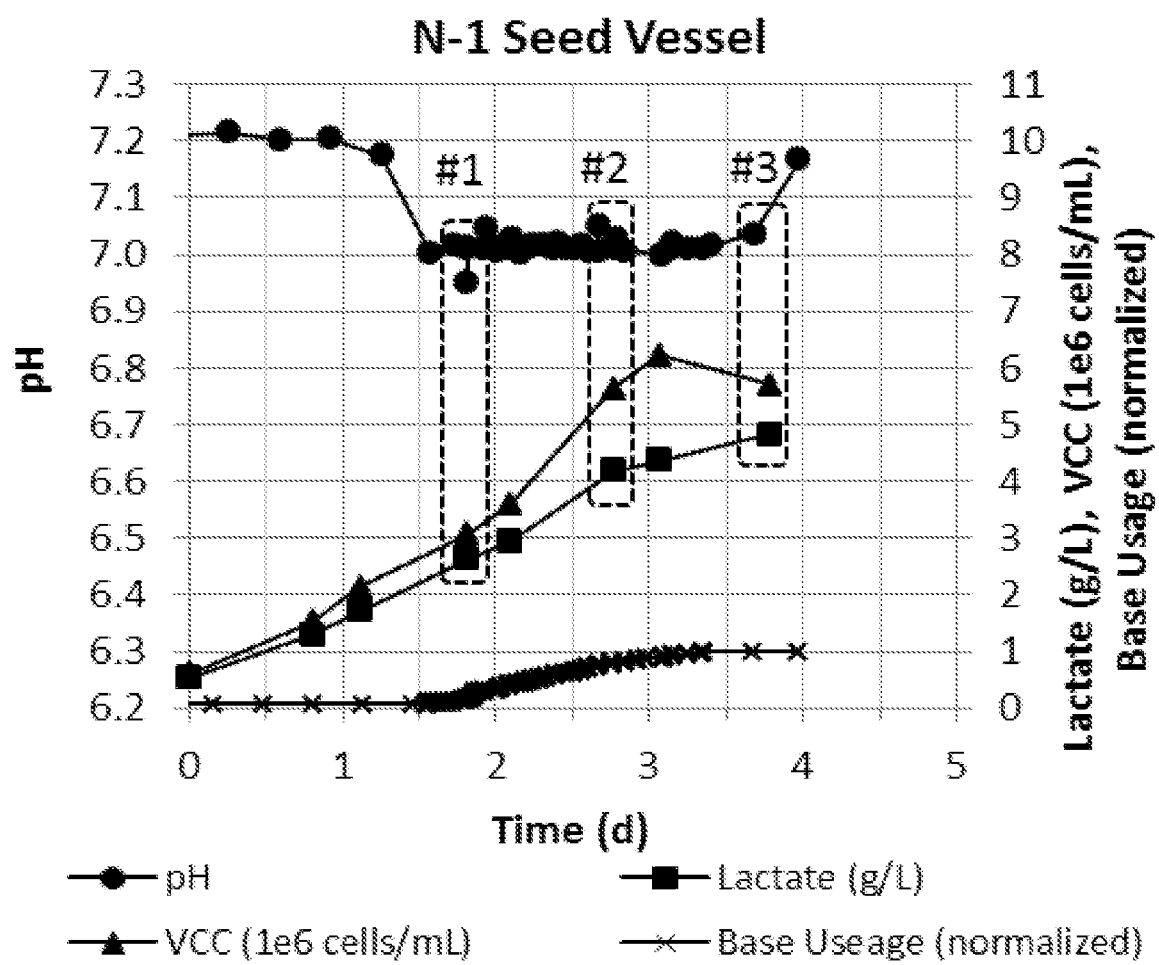
FIGS. 1A-1C: A fusion protein-producing CHO cell line seed vessel was used to inoculate replicate production bioreactors at three different metabolic states (online pH and offline lactate) and viable cell counts (VCC) (FIG. 1A). Base usage normalized to 1 for the seed vessel is also shown. The parameters (time, pH, lactate, VCC, and base) for each cell culture (Condition #1, #2, and #3) from which cells were transferred to production bioreactors are indicated by open rectangles (dotted line). All production bioreactors were run with the same operating conditions. The impact of each seed train and its metabolic state on protein titer (FIG. 1B) and lactate levels (FIG. 1C) in a production bioreactor is shown. Production bioreactor trendlines represent the average of duplicate bioreactors with error bars that represent ± one standard deviation.

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, particular methods and materials are now described. All publications mentioned herein are incorporated herein by reference in their entirety.

Cell Culture

"Batch culture" or "batch mode" as used herein is a phrase that refers to a unit (e.g. culturing vessel) that is filled with cells and with an initial full working volume of medium that is never exchanged. In such a batch culture, all components for cell culturing are supplied to the culturing vessel at the start of the culturing process. The culture usually runs until the nutrients are exhausted or the waste products reach toxic levels and the cells stop growing.

The phrase "seed culture" or "seed train" (also referred to as inoculum train) as used herein includes the inoculation source of a cell population which is allowed to expand in batch culture, or series of batch cultures, until ready for production scale. The seed train expansion process constitutes the initial growth phase of the cells, or inoculum growth phase, following a thaw of frozen cells. The interval between cell thawing and the accumulation of sufficient cell mass to inoculate a production bioreactor constitutes the seed train expansion phase. The cell mass may be scaled up through several bioreactor stages in seed culture, and the cells are grown in cell culture medium under conditions favorable to the survival, growth and viability of the cell culture. It is understood that the seed train is intended to maximize the exponential growth phase, or achieve the maximal growth rate for the particular cell type being cultured. Therefore, passaging of cells from one bioreactor or vessel to another may be one way to achieve maximal growth rate. The precise conditions will vary depending on the cell type, the organism from which the cell was derived, and the nature and character of the expressed polypeptide or protein. A shift to lactate consumption metabolism may occur or be detected in any one of the vessels in a seed train expansion.

The phrase "fed-batch cell culture" or "fed-batch culture" when used herein refers to a batch culture wherein the animal cells and culture medium are supplied to the culturing vessel initially and additional culture nutrients are slowly fed, continuously or in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture can be further distinguished from perfusion culturing insofar as the supernatant is not removed from the culturing vessel during the process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached.

In certain embodiments, perfusion culture as a method for production cell culture of the protein of interest is also contemplated for use in the methods of the present invention. Perfusion cell culture methods for the production of a protein of interest or antibody is known by one of ordinary skill in the art.

The phrase "continuous cell culture" when used herein relates to a technique used to grow cells continually, usually in a particular growth phase. For example, if a constant supply of cells is required, or the production of a particular polypeptide or protein of interest is required, the cell culture may require maintenance in a particular phase of growth. Thus, the conditions must be continually monitored and adjusted accordingly in order to maintain the cells in that particular phase.

The phrase "log phase" as used herein means a period of cell growth typically characterized by cell doubling. The phrases "exponential growth phase" or "exponential phase" are used interchangeably with log phase. In log phase, the number of new cells appearing per unit of time is proportional to the present cell population; hence plotting the natural logarithm of cell number against time produces a straight line. If growth is not limited, doubling will continue at a constant rate so both the number of cells and the rate of population increase doubles with each consecutive time period.

The phrase "stationary phase" as used herein refers to the point where the rate of cell growth equals the rate of cell death. When plotted on a graph, the stationary phase is represented as a plateau, or "smooth," horizontal linear part of the curve.

The term "cell" when used herein includes any cell that is suitable for expressing a recombinant nucleic acid sequence. Cells include those of eukaryotes, such as non-human animal cells, mammalian cells, human cells, or cell fusions such as, for example, hybridomas or quadromas. In certain embodiments, the cell is a human, monkey, ape, hamster, rat or mouse cell. In other embodiments, the cell is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, W138, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g., a PER.C6® cell). In some embodiments, the cell is a CHO cell. In other embodiments, the cell is a CHO K1 cell.

A "cell line" as used herein refers to a cell or cells that are derived from a particular lineage through serial passaging or subculturing of cells. The term "cells" is used interchangeably with "cell population".

Given the current state-of-the-art feeding strategies, CHO cells have achieved cell numbers such as $11 \times 10^6$ cells/mL (at day 8) and titers of, for example, 2.3 g/L human IgG (harvested at day 14), numbers that are typical industrial values for CHO cell fed-batch cultures. See Kim, B J, et al., *Biotechnol Bioeng.* 2012 January; 109(1):137-45. Even more than 10 g/L production of antibody has been reported from CHO cells which have been well established as an important industrial mammalian cell line. See Omasa et al, *Current Pharmaceutical Biotechnology*, 2010, 11: 233-240.

The terms "cell culture medium" and "culture medium" refer to a nutrient solution used for growing mammalian cells that typically provides the necessary nutrients to enhance growth of the cells, such as a carbohydrate energy source, essential amino acids, trace elements, vitamins, etc. Cell culture medium may contain extracts, e.g., serum or peptones (hydrolysates), which supply raw materials that support cell growth. Media may contain yeast-derived or soy extracts, instead of animal-derived extracts. Chemically defined medium refers to a cell culture medium in which all of the chemical components are known. Chemically defined medium is entirely free of animal-derived components, such as serum- or animal-derived peptones.

One aspect of the invention relates to a growth phase wherein cell culture conditions are modified to enhance the growth of recombinant eukaryotic cells. In the growth phase, a basal culture medium and cells are supplied to a culturing vessel in batch.

Figure 3:
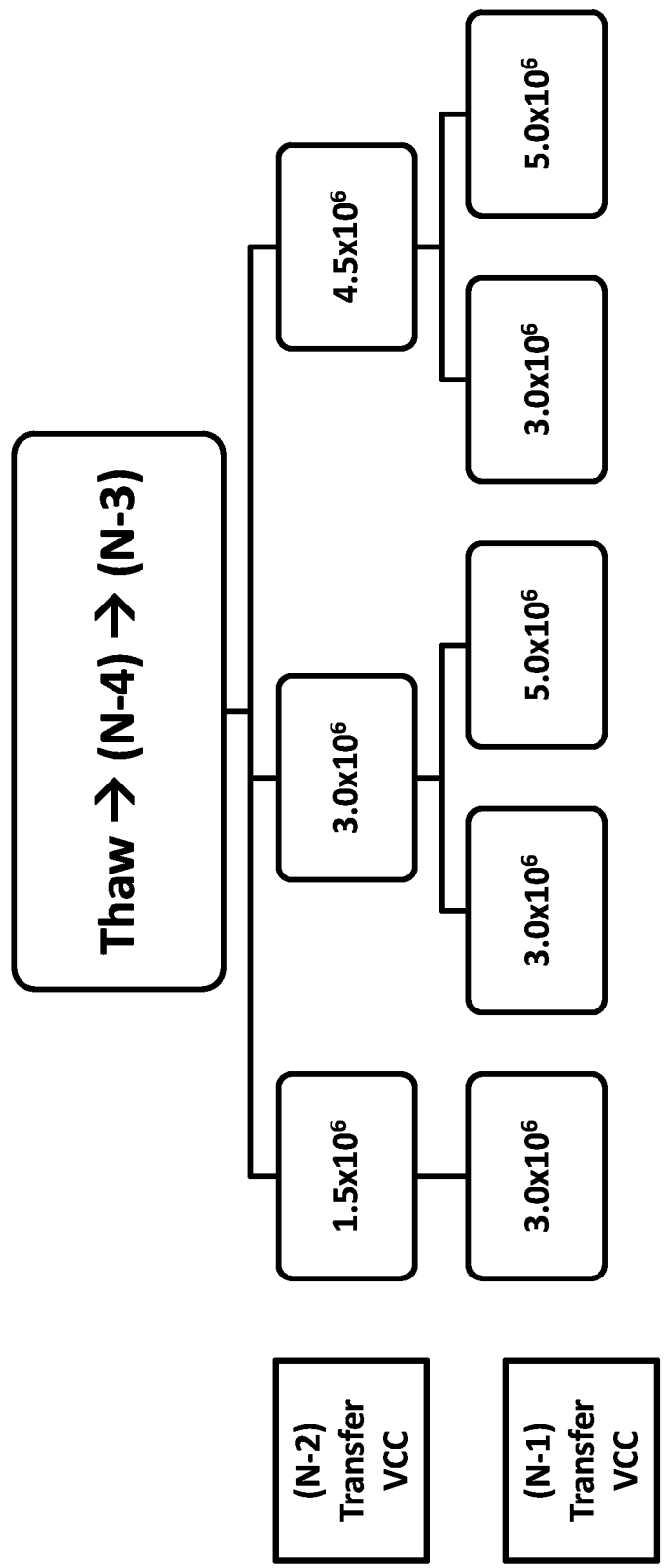
FIG. 3: An exemplary embodiment of the seed train expansion method of the present invention. First, a culture vessel is inoculated with cells (Thaw, or in this example N-5) and the cells are grown in one or more expansion cultures (N-4 and N-3, in this example). Cells from an N-3 growth culture can then be transferred and cultured in an exponential growth phase, a "first seed train culture" (N-2), to a specified viable cell density or a viable cell concentration (VCC). When cells in the N-2 seed train culture reach the specified viable cell concentration (transfer VCC, e.g., $1.5\times10^6$ cells/mL, $3\times10^6$ cells/mL or $4.5\times10^6$ cells/mL), an amount of viable cells can be transferred to another culture vessel and cultured in another exponential growth phase, a "second seed train culture" (N-1) to the specified VCC. When cells in the N-1 seed train culture reach a predetermined viable cell concentration (e.g., $3\times10^6$ cells/mL or $5.0\times10^6$ cells/mL), an amount of viable cells is transferred to a production bioreactor (i.e., production cell culture).

FIG. 3 shows an exemplary embodiment of a seed train expansion method of the present invention. At the outset, a culture vessel is inoculated with cells, such as a previously stored sample of cells (Thaw, i.e. N-5 in this example) and then cells are grown in a series of culture vessels, referred to herein as an "N-X" culture, where "X" is the number of the culture step in a series of culture steps preceding the production culture step. Cells are expanded and transferred to one or more culture vessels (N-4 and N-3 for example) during the seed train expansion. Cells from the N-3 growth culture can be transferred to another culture vessel where the cells are cultured in an exponential growth phase, also referred to herein as a "first seed train culture", a "first cell culture", or a "N-2" culture. In the first seed train culture (i.e., first cell culture), cells are grown to a predetermined viable cell density or viable cell concentration (VCC). When cells in the first seed train culture reach the predetermined VCC (e.g., greater than $3.0 \times 10^6$ cells/mL), an amount of viable cells can be transferred to yet another culture vessel and cultured in an second exponential growth phase, referred to herein as a "second seed train culture", a "second cell culture", or a "N-1" culture. Cells in the second seed train culture (i.e., second cell culture) are cultured to a second predetermined viable cell density or viable cell concentration, e.g., greater than $3.0 \times 10^6$ cells/mL. When cells in the second seed train culture reach the desired viable cell concentration (e.g., $3 \times 10^6$ cells/mL or $5.0 \times 10^6$ cells/mL), an amount of viable cells can be transferred to a production bioreactor (i.e., production cell culture) and subsequently proteins from such cells can be harvested. In certain embodiments, a suitable seeding density for the initial cell growth phase (Thaw, N-5) varies depending on the starting cell line, for example, in the range of 0.2 to $3 \times 10^6$ cells/mL.

Culturing vessels for use in the instant methods include, but are not limited to, well plates, T-flasks, shake flasks, stirred vessels, spinner flasks, hollow fiber, air lift bioreactors, and the like. A suitable cell culturing vessel is a bioreactor. As used herein the phrase "bioreactor" refers to any culturing vessel that is manufactured or engineered to manipulate or control environmental conditions. Such culturing vessels are well known in the art. Bioreactor processes and systems have been developed to optimize gas exchange, to supply sufficient oxygen to sustain cell growth and productivity, and to remove $CO_2$. Maintaining the efficiency of gas exchange is an important criterion for ensuring successful scale up of cell culture and protein production. Such systems are well-known to the person having skill in the art.

In certain embodiments, the production cell culture is carried out in a bench-top scale, e.g. 2 liter (L) scale, or at pilot-scale or production-scale cell culture vessel of greater than 100 L. In other embodiments, the production culture is carried out in a cell culture vessel of about 100 L to about 500 L, about 500 L to about 1000 L, about 1000 L to about 3000 L, about 3000 L to about 10000 L, or greater than 10000 L. In a specific embodiment, the second cell culture is carried out in a 160 L cell culture vessel. In a specific embodiment, the production culture is carried out in a 500 L, 1000 L, 3000 L or 10000 L cell culture vessel.

It is understood that the initial grow phase may be considered the N-8, or N-7, or N-6, or N-5, N-4, or N-3 starting cell culture in the context of a seed train, and the number of passages is chosen by the skilled person in the art. It is also understood that the first cell culture of the methods of the disclosure is at least the N-2 seed train cell culture step, or the seed train culture step prior to the final seed train culture, which is herein referred to as the second cell culture, or N-1 seed train cell culture.

A shift to lactate consumption metabolism may occur or be detected in any one of the vessels in a seed train expansion, whereas the viable cell concentration in any such seed train vessel may reach $3 \times 10^6$ cells/mL, or greater, such as $5.0 \times 10^6$ cells/mL, as is described throughout the disclosure.

According to the present invention, the exponential growth phase or the first seed culture (i.e. first cell culture) is typically followed by a distinct second culture, which is followed by a third distinct cell culture step, known as the polypeptide production phase or production cell culture. In one embodiment, cells undergoing a metabolic shift to lactate consumption in a first cell culture are transferred to a second cell culture. In one embodiment, the second cell culture is carried out in a different culturing vessel from the cell growth phase or first seed culture. In some embodiments, an amount of cells from the second cell culture are transferred to a production cell culture. In certain embodiments, the production cell culture takes place in a production bioreactor. In such embodiments, transferring cells refers to the removal of at least an amount of the cell population from a culture vessel and placing the removed cell population into a distinct cell culture vessel.

In some embodiments, transferring cells refers to removing a volume of a cell culture (containing an amount of cells from this cell culture) and placing the removed volume in a different vessel for use as an inoculum for a subsequent cell culture. In other embodiments, transferring cells refers to maintaining a volume of a cell culture in a culture vessel, and adding medium to a final volume for a subsequent culture. Irrespective of the manner of transfer, the volume of a culture being transferred to a subsequent culture relative to the final volume of the subsequent culture may vary. For example, a volume from the cell culture of a first seed train is from 1% to 80% of the final volume of a second seed train culture, from 10% to 70% of the final volume of the second cell culture, from 20% to 50% of the final volume of the second cell culture, from 30% to 50% of the final volume of the second cell culture, or from 20% to 30% of the final volume of the second cell culture. In other embodiments, the volume from the first cell culture is about 1%, 2%, 5%, 10%, 15%, 20%, 30%, 40%, or 50%, or 60%, or 70% or 80% of the final volume of the second cell culture. In other embodiments, a volume from the cell culture of a second seed train is from 1% to 80% of the final volume of a production cell culture, from 10% to 70% of the final volume of the second cell culture, from 20% to 50% of the final volume of the production cell culture, from 30% to 50% of the final volume of the production cell culture, or from 20% to 30% of the final volume of the production cell culture. In other embodiments, the volume from the second cell culture is about 1%, 2%, 5%, 10%, 15%, 20%, 30%, 40%, or 50%, or 60%, or 70% or 80% of the final volume of the production cell culture.

The phrase "emerge from" or "emerges from" as used herein refers to a change from one phase to another phase, or about to change from one phase to another phase. Emerging from a particular phase, for example a growth phase, includes the time period where measurements indicate that a first phase is slowing down or nearly complete, and the subsequent phase is beginning. Emerging from log phase, for example, indicates that cells are ending log phase, and/or are starting or have reached stationary phase. Growth phases are typically measured by viable cell concentration or viable cell density.

The phrase "cell density" refers to the number of cells per volume of sample (e.g., a cell culture), for example as number of total (viable and dead) cells per mL. The number of cells may be counted manually or by automation, such as with a flow cytometer. Automated cell counters have been adapted to count the number of viable or dead or both viable and dead cells using, for example a standard tryptan blue uptake technique. The phrase "viable cell density" or "viable cell concentration" refers to the number of viable cells per volume of sample (also referred to as "viable cell count"). Any number of well-known manual or automated techniques may be used to determine cell density. Online biomass measurements of the culture may be measured, where the capacitance or optical density is correlated to the number of cells per volume.

For example, cell density or viable cell concentration may be determined using an autosampler for semi-continuous monitoring of a cell culture. Specifically, a first seed train cell culture can be cultured to a predetermined viable cell concentration under continuous or semi-continuous monitoring using a BioProfile® FLEX automated cell culture analyzer (Nova® Biomedical, Waltham, Mass.). Here, sample cell density and cell viability are measured by automated hemocytometry using a trypan blue exclusion assay. The cell sample is then analyzed by high resolution digital optics in the cell culture analyzer and the user is provided with the viable cell concentration.

Final cell density (i.e., viable cell concentration immediately prior to transfer) of a first cell culture, such as first seed train density, varies depending on the starting cell line, and can be, for example, in the range of 1.0 to $10 \times 10^6$ cells/mL.

As provided below, it has been determined that growing cells to a predetermined final seed train viable cell concentration results in a surprising and unexpected metabolic shift to lactate consumption of the cells in culture. In one embodiment of the present methods cells of a first cell culture are cultured to a final seed train density that is at least 3.0 to $10 \times 10^6$ cells/mL prior to transfer of a fraction of such cells to another cell culture. In other embodiments of the present methods, cells of a first cell culture are cultured to a final seed train density that is greater than 3.0 to $10 \times 10^6$ cells/mL prior to transfer of a fraction of such cells to another cell culture. In specific embodiments, a final seed train viable cell concentration of $3.1 \times 10^6$ cells/mL to $5.0 \times 10^6$ cells/mL is reached prior to transfer of at least a portion of the cells in a first cell culture to a second cell culture vessel. In other embodiments, a final seed train viable cell concentration of $3.5 \times 10^6$ cells/mL to $5.0 \times 10^6$ cells/mL is reached prior to transfer of at least a portion of the cells in a first cell culture to a second cell culture vessel. In certain embodiments, a final seed train viable cell concentration of $4.0 \times 10^6$ cells/mL to $5.0 \times 10^6$ cells/mL is reached prior to transfer of at least a portion of the cells in a first cell culture to a second cell culture vessel. In other embodiments of the present methods, cells in a first cell culture are cultured to a viable cell concentration of $3.1 \times 10^6$ cells/mL, $3.2 \times 10^6$ cells/mL. $3.3 \times 10^6$ cells/mL, $3.4 \times 10^6$ cells/mL, $3.5 \times 10^6$ cells/mL, $3.6 \times 10^6$ cells/mL, $3.7 \times 10^6$ cells/mL, $3.8 \times 10^6$ cells/mL, $3.9 \times 10^6$ cells/mL, $4.0 \times 10^6$ cells/mL, $4.1 \times 10^6$ cells/mL, $4.2 \times 10^6$ cells/mL, $4.3 \times 10^6$ cells/mL, $4.4 \times 10^6$ cells/mL, $4.5 \times 10^6$ cells/mL, $4.6 \times 10^6$ cells/mL, $4.7 \times 10^6$ cells/mL, $4.8 \times 10^6$ cells/mL, $4.9 \times 10^6$ cells/mL, $5.0 \times 10^6$ cells/mL $5.1 \times 10^6$ cells/mL, $5.2 \times 10^6$ cells/mL, $5.3 \times 10^6$ cells/mL, $5.4 \times 10^6$ cells/mL, $5.5 \times 10^6$ cells/mL, $5.6 \times 10^6$ cells/mL, $5.7 \times 10^6$ cells/mL, $5.8 \times 10^6$ cells/mL, $5.9 \times 10^6$ cells/mL or $6.0 \times 10^6$ cells/mL prior to transfer of at least a portion of the cells in a first cell culture to a second cell culture.

In certain embodiments, the cell supernatant or cell lysate is harvested following the production phase. In other embodiments, the polypeptide or protein of interest is recovered from the culture medium or cell lysate, using techniques well known in the art.

The properties of the cells and the location of the produced product dictate the method used for growth and production, and consequently the selection of a suitable type of bioreactor or culturing vessel. See Bleckwenn, N A and Shiloach, J. 2004 "Large-scale cell culture" *Curr Protoc Immunol.* 59: Appendix 1U.1-Appendix 1U.44.

Metabolic Shift

The phrase "metabolic shift" when used herein refers to a change in cell metabolism, or use of carbon nutrient sources, from lactate production to net lactate consumption. While not being bound to any one theory, the most common carbon nutrient sources in serum-free media are glucose and glutamine, which support rapid cell growth. Glucose may be completely oxidized to $CO_2$ and $H_2O$, or, based on the availability of oxygen, be converted to lactate such as in aerobic glycolysis. Fast growing cells consume glucose and glutamine quickly, leading to incomplete oxidative metabolism and, hence, excess lactate production. Carbohydrate metabolism may switch to lactate consumption, and thus reduce the accumulation of lactate.

The phrase "lactate consumption" when used herein refers to the use of lactate as a carbon source in cell metabolism.

The phrase "net lactate consumption" when used herein refers to lactate consumption whereas cells are simultaneously consuming lactate and producing lactate as a byproduct of cell metabolism, and overall rate of consumption is greater than or equal to the rate of production of lactate. When net lactate consumption is increased, overall accumulation of lactate in a cell culture medium is decreased.

Upon initiation of a fed-batch culture, accumulation of lactate, and possibly ammonia, cause the viability of cells to decrease quickly. It has been reported that in fed-batch cultures that did not metabolically shift, none could achieve over 90% viability when the cell concentration had reached its maximum. See Xie and Wang, 1994, *Biotechnol. Bioeng.* 43(11):1175-1189. Such a metabolic shift, although desirable for optimum process performance, is neither generic nor easily controlled. See Zagari, et al., 2013, *New Biotechnol.* 30(2):238-245. The inventors have discovered that the time and conditions for transfer of cells from a cell culture, for example, a first seed culture or second seed train culture, will switch the cells in culture to metabolic lactate consumption and confer a metabolic preference, or metabolic phenotype, for consumption of lactate, which has a significant impact on final protein titer.

In one aspect, it has been determined, unexpectedly, that cells cultured for a longer period of time in a first batch culture will switch to lactate consumption and confer a metabolic preference, or metabolic phenotype, for consumption of lactate. It is an objective of this invention to create cells in a constant metabolically shifted state, hence cells with a metabolic memory for lactate consumption. The methods of the invention are well-suited for preconditioning cells into a metabolically shifted state such that the cells may be used in any subsequent cell culture where lactate consumption is preferred.

In another aspect, it has been determined that culturing cells to a final seed train density that is greater than $3.0 \times 10^6$ cells/mL prior to transfer of a fraction of such cells to another cell culture results in a surprising and unexpected metabolic shift to lactate consumption of the cells in culture. This viable cell concentration mediated shift to lactate consumption has beneficial effects on production culture, such as reduced peak and final lactate concentrations, a reduced lactate accumulation rate and increased maximum protein titer in the production cell culture. Therefore, a method of culturing cells is provided that includes culturing cells in a first cell culture, determining that a metabolic shift to lactate consumption in the cells has occurred in the first cell culture, transferring an amount of cells from the first cell culture to a second cell culture after the metabolic shift to lactate consumption in the cells has occurred, then culturing cells in the second cell culture to achieve a predetermined viable cell concentration, and subsequently transferring an amount of cells from the second cell culture to a production cell culture, wherein viable cell density is increased in the production cell culture. In certain embodiments, cells in the first cell culture are cultured to a viable cell concentration of greater than $3.0 \times 10^6$ cells/mL, which results in an early shift to lactate consumption. In other embodiments, a shift to lactate consumption is achieved when cells in the first cell culture are cultured to a viable cell concentration of $3.1 \times 10^6$ cells/mL to $5.0 \times 10^6$ cells/mL prior to transfer of at least a portion of the cells in the first cell culture to a second cell culture. In another embodiment, a shift to lactate consumption is achieved when cells in the first cell culture are cultured to a viable cell concentration of $3.5 \times 10^6$ cells/mL to $5.0 \times 10^6$ cells/mL prior to transfer of at least a portion of the cells in the first cell culture to a second cell culture. In certain embodiments, cells in the first cell culture are cultured to a viable cell concentration of $4.0 \times 10^6$ cells/mL to $5.0 \times 10^6$ cells/mL prior to transfer of at least a portion of the cells in the first cell culture to a second cell culture vessel. In other embodiments, cells in the first cell culture are cultured to a viable cell concentration of $3.5 \times 10^6$ cells/mL, $4.0 \times 10^6$ cells/mL, $4.5 \times 10^6$ or $5.0 \times 10^6$ cells/mL prior to transfer of at least a portion of the cells in the first cell culture to a second cell culture. In other embodiments of the present methods, cells in the first cell culture are cultured to a final viable cell concentration, which results in a shift to lactate consumption, of $3.1 \times 10^6$ cells/mL, $3.2 \times 10^6$ cells/mL, $3.3 \times 10^6$ cells/mL, $3.4 \times 10^6$ cells/mL, $3.5 \times 10^6$ cells/mL, $3.6 \times 10^6$ cells/mL, $3.7 \times 10^6$ cells/mL, $3.8 \times 10^6$ cells/mL, $3.9 \times 10^6$ cells/mL, $4.0 \times 10^6$ cells/mL, $4.1 \times 10^6$ cells/mL, $4.2 \times 10^6$ cells/mL, $4.3 \times 10^6$ cells/mL, $4.4 \times 10^6$ cells/mL, $4.5 \times 10^6$ cells/mL, $4.6 \times 10^6$ cells/mL, $4.7 \times 10^6$ cells/mL, $4.8 \times 10^6$ cells/mL, $4.9 \times 10^6$ cells/mL, $5.0 \times 10^6$ cells/mL $5.1 \times 10^6$ cells/mL, $5.2 \times 10^6$ cells/mL, $5.3 \times 10^6$ cells/mL, $5.4 \times 10^6$ cells/mL, $5.5 \times 10^6$ cells/mL, $5.6 \times 10^6$ cells/mL, $5.7 \times 10^6$ cells/mL, $5.8 \times 10^6$ cells/mL, $5.9 \times 10^6$ cells/mL or $6.0 \times 10^6$ cells/mL, and at least a portion of the cells in a first cell culture are subsequently transferred to a second cell culture.

In a specific embodiment, cells in a first cell culture are cultured to a predetermined viable cell concentration of greater than $3.0 \times 10^6$ cells/mL cells, which induces an early shift to lactate consumption; and subsequently, a portion of the cells from the first cell culture are transferred to a second cell culture and cultured to a predetermined viable cell concentration (e.g., at least $3.0 \times 10^6$ cells/mL) prior to transferring a portion of the cells in the second cell culture to a production culture.

In certain embodiments, the method further provides detecting a reduced rate of lactate accumulation in a first cell culture prior to transfer to a second cell culture, as compared to the rate of lactate accumulation determined in an otherwise identical cell culture under otherwise identical conditions except that transferring cells to the second cell culture occurs prior to a metabolic shift to lactate consumption has occurred in the first cell culture.

In another embodiment of the invention, cells in a first cell culture are cultured to a predetermined viable cell culture concentration and a metabolic shift to lactate consumption is observed in the cells from the first cell culture, then a portion of cells from the first cell culture is transferred to a second cell culture and cultured to achieve a viable cell concentration of greater than $3.0 \times 10^6$ cells/mL prior to transfer to a production cell culture. In certain embodiments, a metabolic shift to lactate consumption is observed in the cells in the second cell culture. In certain embodiments, a shift to lactate consumption is achieved when cells in a second cell culture are cultured to a viable cell concentration of greater than $3.0 \times 10^6$ cells/mL to $5.0 \times 10^6$ cells/mL prior to transferring at least a portion of the cells in the second cell culture to a production cell culture. In other embodiments, cells in a second cell culture are cultured to a viable cell concentration of $3.1 \times 10^6$ cells/mL to $5.0 \times 10^6$ cells/mL prior to transfer of at least a portion of the cells in the second cell culture to a production cell culture. In another embodiment, cells in a second cell culture are cultured to a viable cell concentration of $3.5 \times 10^6$ cells/mL to $5.0 \times 10^6$ cells/mL prior to transfer of at least a portion of the cells in the second cell culture to a production cell culture. In certain embodiments, cells in a second cell culture are cultured to a viable cell concentration of $4.0 \times 10^6$ cells/mL to $5.0 \times 10^6$ cells/mL prior to transfer of at least a portion of the cells in the second cell culture to a production cell culture. In other embodiments, cells in a second cell culture are cultured to a viable cell concentration of $3.5 \times 10^6$ cells/mL, $4.0 \times 10^6$ cells/mL, $4.5 \times 10^6$ or $5.0 \times 10^6$ cells/mL prior to transfer of at least a portion of the cells in the second cell culture to a production cell culture. In other embodiments, cells in a second cell culture are cultured to a final viable cell concentration of $3.1 \times 10^6$ cells/mL, $3.2 \times 10^6$ cells/mL, $3.3 \times 10^6$ cells/mL, $3.4 \times 10^6$ cells/mL, $3.5 \times 10^6$ cells/mL, $3.6 \times 10^6$ cells/mL, $3.7 \times 10^6$ cells/mL, $3.8 \times 10^6$ cells/mL, $3.9 \times 10^6$ cells/mL, $4.0 \times 10^6$ cells/mL, $4.1 \times 10^6$ cells/mL, $4.2 \times 10^6$ cells/mL, $4.3 \times 10^6$ cells/mL, $4.4 \times 10^6$ cells/mL, $4.5 \times 10^6$ cells/mL, $4.6 \times 10^6$ cells/mL, $4.7 \times 10^6$ cells/mL, $4.8 \times 10^6$ cells/mL, $4.9 \times 10^6$ cells/mL, $5.0 \times 10^6$ cells/mL $5.1 \times 10^6$ cells/mL, $5.2 \times 10^6$ cells/mL, $5.3 \times 10^6$ cells/mL, $5.4 \times 10^6$ cells/mL, $5.5 \times 10^6$ cells/mL, $5.6 \times 10^6$ cells/mL, $5.7 \times 10^6$ cells/mL, $5.8 \times 10^6$ cells/mL, $5.9 \times 10^6$ cells/mL, $6.0 \times 10^6$ cells/mL or greater, and at least a portion of the cells in a second cell culture are subsequently transferred to a production cell culture.

In certain embodiments, the instant method further provides detecting a reduced rate of lactate accumulation in a second cell culture prior to transfer to the production cell culture, as compared to the rate of lactate accumulation determined in an otherwise identical cell culture under otherwise identical conditions except transferring cells to the production cell culture occurs prior to a metabolic shift has occurred in the second cell culture.

In a specific embodiment, cells in a first cell culture are cultured to a viable cell concentration of greater than $3.0 \times 10^6$ cells/mL cells, which induces an early shift to lactate consumption; and subsequently, a portion of the cells from the first cell culture are transferred to a second cell culture and cultured to a viable cell concentration of at least $3.0 \times 10^6$ cells/mL prior to transferring a portion of the cells in the second cell culture to a production culture. In some embodiments, cells in a first cell culture are cultured to a viable cell concentration of greater than $3.0 \times 10^6$ cells/mL to $5.0 \times 10^6$ cells/mL prior to transferring at least a portion of the cells in the first cell culture to a second cell culture. In other embodiments, cells in a first cell culture are cultured to a viable cell concentration of $3.1 \times 10^6$ cells/mL to $5.0 \times 10^6$ cells/mL prior to transfer of at least a portion of the cells in the first cell culture to a second cell culture. In another embodiment, cells in a first cell culture are cultured to a viable cell concentration of $3.5 \times 10^6$ cells/mL to $5.0 \times 10^6$ cells/mL prior to transfer of at least a portion of the cells in the first cell culture to a second cell culture. In certain embodiments, cells in a first cell culture are cultured to a viable cell concentration of $4.0 \times 10^6$ cells/mL to $5.0 \times 10^6$ cells/mL prior to transfer of at least a portion of the cells in the first cell culture to a second cell culture. In other embodiments, cells in a first cell culture are cultured to a viable cell concentration of $3.5 \times 10^6$ cells/mL, $4.0 \times 10^6$ cells/mL, $4.5 \times 10^6$ or $5.0 \times 10^6$ cells/mL prior to transfer of at least a portion of the cells in the first cell culture to a second cell culture. In other embodiments, cells in a first cell culture are cultured to a final viable cell concentration of $3.1 \times 10^6$ cells/mL, $3.2 \times 10^6$ cells/mL, $3.3 \times 10^6$ cells/mL, $3.4 \times 10^6$ cells/mL, $3.5 \times 10^6$ cells/mL, $3.6 \times 10^6$ cells/mL, $3.7 \times 10^6$ cells/mL, $3.8 \times 10^6$ cells/mL, $3.9 \times 10^6$ cells/mL, $4.0 \times 10^6$ cells/mL, $4.1 \times 10^6$ cells/mL, $4.2 \times 10^6$ cells/mL, $4.3 \times 10^6$ cells/mL, $4.4 \times 10^6$ cells/mL, $4.5 \times 10^6$ cells/mL, $4.6 \times 10^6$ cells/mL, $4.7 \times 10^6$ cells/mL, $4.8 \times 10^6$ cells/mL, $4.9 \times 10^6$ cells/mL, $5.0 \times 10^6$ cells/mL $5.1 \times 10^6$ cells/mL, $5.2 \times 10^6$ cells/mL, $5.3 \times 10^6$ cells/mL, $5.4 \times 10^6$ cells/mL, $5.5 \times 10^6$ cells/mL, $5.6 \times 10^6$ cells/mL, $5.7 \times 10^6$ cells/mL, $5.8 \times 10^6$ cells/mL, $5.9 \times 10^6$ cells/mL, $6.0 \times 10^6$ cells/mL or greater, and at least a portion of the cells in the first cell culture are subsequently transferred to a second cell culture. In any of the foregoing embodiments, cells in the second cell culture are cultured to a viable cell concentration of greater than $3.0 \times 10^6$ cells/mL to $5.0 \times 10^6$ cells/mL prior to transferring at least a portion of the cells in the second cell culture to a production cell culture. In other embodiments, cells in the second cell culture are cultured to a viable cell concentration of $3.1 \times 10^6$ cells/mL to $5.0 \times 10^6$ cells/mL prior to transfer of at least a portion of the cells in the first cell culture to a production cell culture. In another embodiment, cells in the second cell culture are cultured to a viable cell concentration of $3.5 \times 10^6$ cells/mL to $5.0 \times 10^6$ cells/mL prior to transfer of at least a portion of the cells in the second cell culture to a production cell culture. In certain embodiments, cells in the second cell culture are cultured to a viable cell concentration of $4.0 \times 10^6$ cells/mL to $5.0 \times 10^6$ cells/mL prior to transfer of at least a portion of the cells in the second cell culture to a production cell culture. In other embodiments, cells in the second cell culture are cultured to a viable cell concentration of $3.5 \times 10^6$ cells/mL, $4.0 \times 10^6$ cells/mL, $4.5 \times 10^6$ or $5.0 \times 10^6$ cells/mL prior to transfer of at least a portion of the cells in the second cell culture to a production cell culture. In other embodiments, cells in the second cell culture are cultured to a final viable cell concentration of $3.1 \times 10^6$ cells/mL, $3.2 \times 10^6$ cells/mL, $3.3 \times 10^6$ cells/mL, $3.4 \times 10^6$ cells/mL, $3.5 \times 10^6$ cells/mL, $3.6 \times 10^6$ cells/mL, $3.7 \times 10^6$ cells/mL, $3.8 \times 10^6$ cells/mL, $3.9 \times 10^6$ cells/mL, $4.0 \times 10^6$ cells/mL, $4.1 \times 10^6$ cells/mL, $4.2 \times 10^6$ cells/mL, $4.3 \times 10^6$ cells/mL, $4.4 \times 10^6$ cells/mL, $4.5 \times 10^6$ cells/mL, $4.6 \times 10^6$ cells/mL, $4.7 \times 10^6$ cells/mL, $4.8 \times 10^6$ cells/mL, $4.9 \times 10^6$ cells/mL, $5.0 \times 10^6$ cells/mL cells/mL $5.1 \times 10^6$ cells/mL, $5.2 \times 10^6$ cells/mL, $5.3 \times 10^6$ cells/mL, $5.4 \times 10^6$ cells/mL, $5.5 \times 10^6$ cells/mL, $5.6 \times 10^6$ cells/mL, $5.7 \times 10^6$ cells/mL, $5.8 \times 10^6$ cells/mL, $5.9 \times 10^6$ cells/mL, $6.0 \times 10^6$ cells/mL or greater, and at least a portion of the cells in a second cell culture are subsequently transferred to a production cell culture.

The methods of the invention are well-suited for preconditioning cells into a metabolically shifted state such that the cells may be used in any subsequent cell culture where lactate consumption is preferred.

In one embodiment, overall accumulation of lactate decreases in a first or second cell culture using the present methods. In some embodiments, net lactate consumption is achieved during a first cell culture, for example, net lactate consumption is achieved on or after 2 days, 3 days, 4 days, or 5 days of cell growth in a first cell culture. In other embodiments, net lactate consumption is achieved during a second cell culture, for example, net lactate consumption is achieved on or after 2 days, 3 days, 4 days, or 5 days of cell growth in a second cell culture. In other embodiments, net lactate consumption is achieved in a first seed train cell culture when a viable cell concentration is greater than $3.0 \times 10^6$ cells/mL. In other embodiments, net lactate consumption is achieved in a second seed train cell culture when a viable cell concentration is greater than $3.0 \times 10^6$ cells/mL. In more embodiments, the decrease in accumulation of lactate is a reduction in peak lactate concentration in a first or second cell culture. In certain embodiments, the reduction in peak lactate concentration occurs in a second cell culture on or after 5 days of cell growth in the second cell culture. In other embodiments, peak lactate concentration in a first or second cell culture is less than about 6 g/L, 5 g/L, 4 g/L, 3 g/L, 2 g/L, or less than about 1 g/L. In certain embodiments, culturing cells in a first or a second seed train culture to a viable cell concentration that is greater than $3.0 \times 10^6$ cells/mL results in a reduction in peak lactate concentration. In certain embodiments, the reduced lactate concentration in a first or second seed train cell culture is less than about 6 g/L, 5 g/L, 4 g/L, 3 g/L, 2 g/L, or less than about 1 g/L.

In some embodiments, metabolically shifted cells produce at least a 0.5-fold, 0.6-fold, 0.7-fold, 0.8-fold, 0.9-fold, 1-fold, 1.1-fold, 1.2-fold, 1.3-fold, 1.4-fold, 1.5-fold, 1.6-fold, 1.7-fold, 1.8-fold, 1.9-fold, 2-fold, 1.1-fold, 2.2-fold, 2.3-fold, 2.4-fold, 2.5-fold, 2.6-fold, 2.7-fold, 2.8-fold, 2.9-fold, or 3-fold, or 4-fold, or 5-fold, or up to 10-fold lower lactate concentration values in a second cell culture. In some further embodiments, lower lactate concentration values in a second cell culture or overall decreased accumulation of lactate in the second cell culture is compared to that determined in an otherwise identical cell culture under otherwise identical conditions except transferring cells to the second cell culture is before a metabolic shift has occurred in the first cell culture. In still other embodiments, overall accumulation of lactate decreases in the second cell culture on or after 5 days of cell growth in the second cell culture.

In another embodiment, overall product titer increases in a production culture using the present methods. In specific embodiments, metabolically shifted cells produce at least a 0.5-fold, 0.6-fold, 0.7-fold, 0.8-fold, 0.9-fold, 1-fold, 1.1-fold, 1.2-fold, 1.3-fold, 1.4-fold, 1.5-fold, 1.6-fold, 1.7-fold, 1.8-fold, 1.9-fold, 2-fold, 1.1-fold, 2.2-fold, 2.3-fold, 2.4-fold, 2.5-fold, 2.6-fold, 2.7-fold, 2.8-fold, 2.9-fold, or 3-fold, or 4-fold, or 5-fold, or up to 10-fold higher product titer in a production cell culture. In still other embodiments, higher protein titer values in a production cell culture is compared to that determined in an otherwise identical cell culture under otherwise identical conditions except transferring cells to either the second cell culture or the production titer occurs before a metabolic shift has occurred.

Optimizing metabolic control of cells in culture prior to the fed-batch or production stage has many advantages. Metabolic shift to lactate consumption in a first culture may be determined by multiple parameters. Determining a metabolic shift comprises a number of methods known to the skilled artisan for determining the metabolic state of growing cells.

For example, measurement of lactate concentration values in a first cell culture may be done by a variety of bioassay systems and kits well known to the person skilled in the art, such as analyzers using electrochemistry (e.g. BioProfile® FLEX, nova Biomedical, Waltham, Mass.), or Raman spectroscopy, and may be used for offline or online monitoring of lactate accumulation in cell culture.

It is understood that lactate accumulation has a detrimental effect on cell culture, and subsequently has a negative effect on protein product yield.

Figure 4:
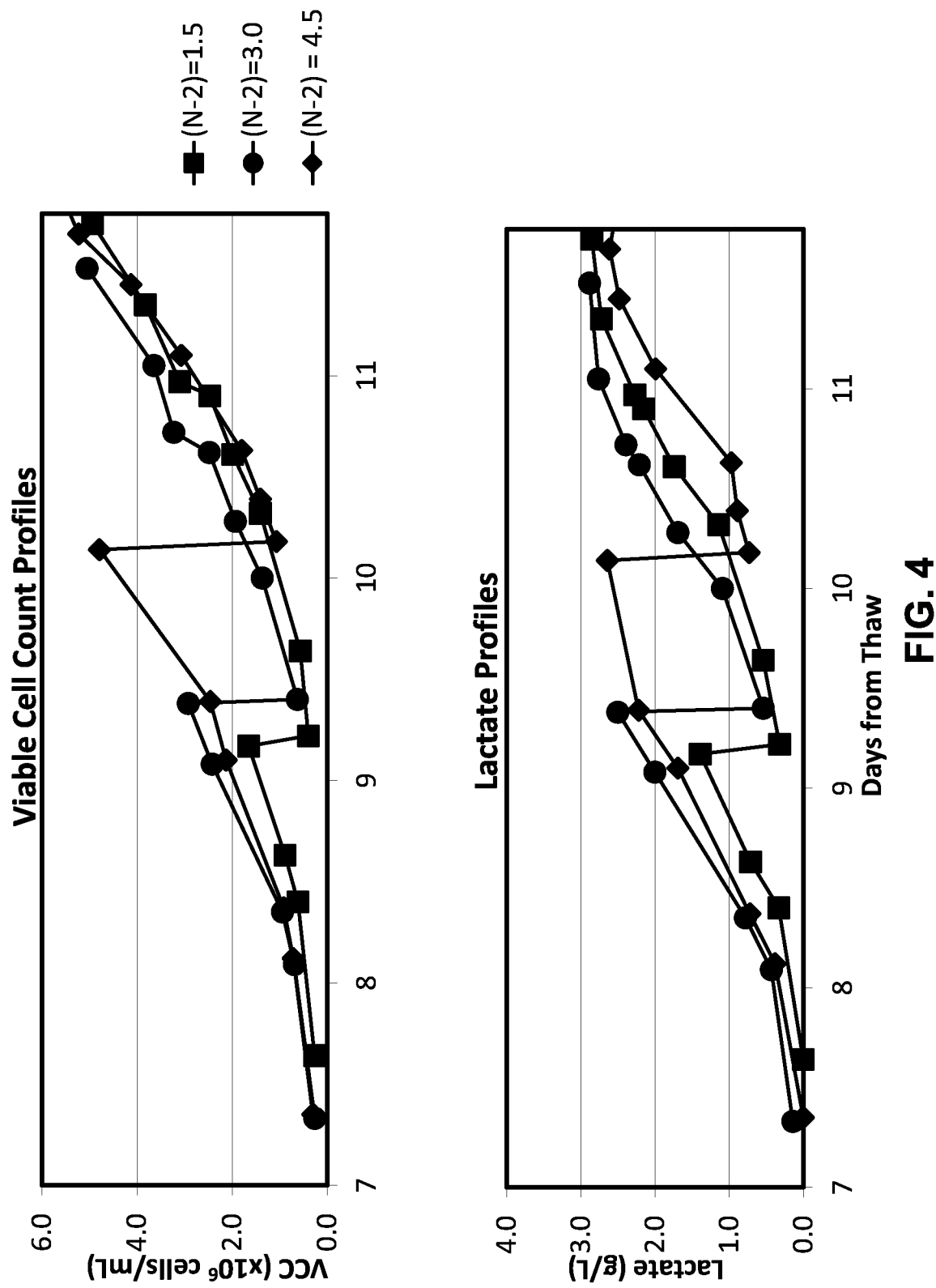
FIG. 4: Viable cell count profiles and lactate accumulation profiles for seed train bioreactors. (Top) Cell are grown in a first seed train culture (N-2) to a representative high viable cell concentration of $4.5\times10^6$ cells/mL, which results in a reduced rate of lactate accumulation. Cell growth is unaffected in both the first seed train culture (N-2) and the second seed train culture step (N-1). (Bottom) Lower peak lactate concentrations in a second seed train culture are exhibited when the rate of lactate accumulation slows in the first seed train culture step (N-2).

In one embodiment, the metabolic shift is determined when the net accumulation of lactate in a cell culture slows or ceases. As shown in FIG. 4, culturing cells in a seed train culture to a viable cell concentration of greater than $3.0 \times 10^6$ cells/mL results in a reduced rate of lactate accumulation.

In one embodiment, the metabolic shift to lactate consumption is detected by lactate measurements in a first cell culture. In some embodiments, the metabolic shift is determined in a first cell culture when a plateau, or essentially horizontal line, is determined on a graph representing the measurement of consecutive lactate concentration values in the culture. In another embodiment, the metabolic shift to lactate consumption is detected by lactate measurements in a second cell culture. In some embodiments, the metabolic shift is determined in a second cell culture when a plateau, or essentially horizontal line, is determined on a graph representing the measurement of consecutive lactate concentration values in the culture. In other embodiments, the lactate concentration value remains below the upper tolerance limit for consecutive measurements. In still other embodiments, the upper tolerance limit for lactate concentration is no greater than 4 g/L. It is understood that lactate levels plateau when the cells undergo net lactate consumption.

In other embodiments, determining the metabolic shift comprises measuring lactate in a first seed train cell culture or a second seed train culture at intervals, and determining that the lactate level is below a predetermined upper limit for consecutive intervals, thereby determining that the metabolic shift to lactate consumption in the cells has occurred.

pH management and control is an important aspect of maintaining cells in a bioreactor culture. The growth of most cells is optimal within narrow limits of pH. Generally, cell culture is maintained at a neutral pH of 7.0, within a range of upper and lower set-point values. Set point values are determined by the person skilled in the art depending on the particular cell line in culture, the medium composition and the optimal conditions for growth for that cell. As used herein, the expression "neutral pH" means a pH of about 6.85 to about 7.4. The expression "neutral pH" includes pH values of about 6.85, 6.9, 6.95, 7.0, 7.05, 7.1, 7.15, 7.2, 7.25, 7.3, 7.35, and 7.4.

On-line, or "real-time", pH monitoring and addition of base may be accomplished by any number of methods well-known to the person skilled in the art. In an on-line system, real-time measurements of biological and chemical parameters in the cell culture by direct connection to an analyzer provide feedback in order to carry out additional actions, for example adding base or adding nutrients to the culture medium. Off-line measurements may also be done whereas periodic sampling and manual operator intervention takes place. Continuous measurement of pH allows cell medium to be monitored and base is added, for example, if acidity reaches a lower set point value outside of tolerance limits. If the pH reaches the set upper tolerance limits (i.e. becomes too basic), $CO_2$ may be added.

On-line monitoring may be done by a variety of methods. Electrodes, such as flow-through electrodes, are commonly used to measure pH, or other parameters such as dissolved $O_2$ ($dO_2$) and temperature, in cell culture medium. Such flow-through electrodes plug directly into any standard strip chart recorder for continuous recording or can be interfaced to any standard laboratory pH or millivolt meter. pH may also be measured by means of an optical measurement with the use of a fluorescent sensor spot mounted in the bioreactor.

Any such monitoring system will integrate a tolerance (or dead-band) limit around set point upper and lower values. The dead-band prevents the dosing system from too rapidly switching on and off. During pH control, no dosing or titration will take place if the pH deviation from the set point is within the tolerance limits. If the pH measurement values are larger than the lower tolerance limit (acidic), then a liquid base (e.g. KOH, NaOH, $NaHCO_3$) or $NH_3$ gas will be added. If the pH measurement values are above the upper tolerance limit (basic), an acid or $CO_2$ gas will be added. The pH set-point and control strategy, e.g., dead-band, are linked to multiple parameters such as dissolved $CO_2$, base consumption for pH control, and therefore, osmolality. See, e.g., Li, F., et al., 2010, *mAbs* 2(5):466-479.

In one embodiment, the metabolic shift is determined in a cell culture when addition (i.e. titration) of base stops. Trending of base includes on-line trending wherein an automated monitoring method may be utilized to determine pH and the periodic addition of base. In the present method, the pH set points may vary but the rise in pH off the lower dead-band are indicative of metabolic shift in the cell culture being analyzed. Online and manual methods of measuring base trending are known in the art, including methods to monitor the weight of the vessel, or the flow rate of the pump to detect base addition or stoppage of base addition.

In another embodiment, the metabolic shift is determined in a cell culture when the addition of base is no longer necessary to raise the pH above the lower tolerance limit.

In some embodiments, the metabolic shift is determined in a culture when the pH value increases without addition of base. In other embodiments, the pH value increases above the lower tolerance limit for consecutive measurements.

In other embodiments, determining the metabolic shift comprises: (a) tuning a pH detection instrument to detect the noise level in a cell culture, (b) continuously measuring pH in the cell culture at regular intervals, (c) adding base as necessary to maintain pH above a predetermined lower limit, (d) determining that the pH is above the predetermined lower limit for several consecutive intervals, and (e) ceasing the addition of base, thereby determining that the metabolic shift to lactate consumption in the cells has occurred.

In one embodiment, the lower tolerance limit is a pH of 6.5 to 7.1. In specific embodiments lower tolerance limit is a pH of 6.5, 6.55, 6.6, 6.65, 6.7, 6.75, 6.8, 6.85, 6.9, 6.95, 7.0, 7.05 or about 7.1.

In some embodiments, the metabolic shift to lactate consumption is detected by indicators or products of cell metabolism in the first cell culture. One such indicator of cell metabolism is oxygen consumption. See Zagari, et al., 2013, *New Biotechnol.* 30(2):238-245. An accurate measure of the rate of oxygen depletion in cell culture medium can be used to determine, the presence of viable cells in the culture following inoculation, as well as the rate of growth of the cells in culture. See, e.g., U.S. Pat. Nos. 6,165,741 and 7,575,890. Measurement of oxygen consumption is well-known in the art.

Other indicators of cell metabolism, such as enzymes and metabolites, may be measured by proteomic or metabolic techniques, such as immunological arrays, nuclear magnetic resonance (NMR) or mass spectrometry. Metabolites, such as glysine, tryptophan, phenylalanine, adenine, palmitic acid, glutamic acid, methionine and asparagine have been correlated with an increase of cellular biomass. See, e.g., Jain, M., et al, Science. 2012 May 25; 336(6084): 1040-1044. doi:10.1126/science.1218595; and De la Luz-Hdez, K., 2012, Metabolomics and Mammalian Cell Culture, Metabolomics, Dr Ute Roessner (Ed.), ISBN: 978-953-51-0046-1, InTech, www.intechopen.com/books/metabolomics/metabolomics-and-mammalian-cell-cultures. Any number of molecular changes that coincide with or directly lead to metabolic shift in the first cell culture may be utilized to determine that a metabolic shift has occurred.

Protein Production

The methods of the invention produce a protein or polypeptide of interest in a cell culture. To enable protein production in the methods of the invention, cells are engineered to recombinantly express the polypeptide or protein of interest.

Cells are transferred to a production culture, after the metabolic shift to lactate consumption in the cells has occurred, and will be maintained in the production cell culture for a period of time so that the polypeptide or protein accumulates in the cell culture.

As used herein, a "polypeptide" is a single linear polymer chain of amino acids bonded together by peptide bonds between the carboxyl and amino groups of adjacent amino acid residues. The term "protein" may also be used to describe a large polypeptide, such as a seven transmembrane spanning domain protein, with a particular folded or spatial structure. As such, the term "protein" is meant to include quaternary structures, ternary structures and other complex macromolecules composed of at least one polypeptide. If the protein is comprised of more than one polypeptide that physically associate with one another, then the term "protein" as used herein refers to the multiple polypeptides that are physically coupled and function together as the discrete unit. The term "protein" includes polypeptide.

Examples of polypeptides and proteins produced by the methods of the invention include antibodies, fusion proteins, Fc-fusion proteins, receptors, receptor-Fc fusion proteins, and the like.

The term "immunoglobulin" refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See, for instance, Fundamental Immunology Ch. 7 Paul, W., ed., 2nd ed. Raven Press, N. Y. (1989). Briefly, each heavy chain typically comprises a heavy chain variable region (abbreviated herein as $V_H$ or VH) and a heavy chain constant region ($C_H$). The heavy chain constant region typically comprises three domains, $C_H1$, $C_H2$, and $C_H3$. The $C_H1$ and $C_H2$ domains are linked by a hinge. Each light chain typically comprises a light chain variable region (abbreviated herein as $V_L$ or VL) and a light chain constant region. There are two types of light chains in humans, and other mammals: kappa (κ) chain and lambda (λ) chain. The light chain constant region typically comprises one domain ($C_L$). The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus (N-terminus) to carboxy-terminus (C-terminus) in the following order: FR1, CDR1, FR2, CDR2, FR3, CDR3, FR4. See also Chothia and Lesk *J. Mol. Biol.* 196, 901-917 (1987). Typically, the numbering of amino acid residues in this region is according to IMGT, Sequences of Proteins of Immunological Interest, 5th Ed. Public Health Service, National Institutes of Health, Bethesda, Md. (1991), or by the EU numbering system of Kabat (also known as "EU numbering" or "EU index"), e.g., as in Kabat, E. A. et al. Sequences of Proteins of Immunological interest. $5^{th}$ ed. US Department of Health and Human Services, NIH publication No. 91-3242 (1991).

The term "Fc" refers to a portion of a heavy chain constant region that comprises at least the CH2 and CH3 domains that typically bind to an Fc receptor e.g., an FcγR, namely FcγRI (CD64), FcγRII (CD32), FcγRIII (CD16) or an FcRn, i.e., a neonatal Fc receptor. It is understood that an Fc-fusion protein may contain all or part of a native Fc domain or contain deletions, substitutions, and/or insertions or other modifications that render it unable to bind any Fc receptor, therefore rendering the domain non-functional or "effectorless" in terms of its typical biological function as achieved through an Fc receptor.

The term "antibody" (Ab) as used herein, refers to an immunoglobulin molecule, or a derivative thereof, which has the ability to specifically bind to an antigen. The variable regions of the heavy and light chains of the immunoglobulin molecule contain a binding domain that interacts with an antigen as outlined above under "immunoglobulin". An antibody may also be a bispecific antibody, diabody, or similar molecule. See, e.g., Holliger, et al., 1993, *PNAS USA* 90(14), 6444-8. Further, it has been shown that the antigen-binding function of an antibody may be performed by fragments of a full-length antibody, i.e. "antigen-binding fragments" or "antigen-binding proteins". As with full antibody molecules, antigen-binding proteins may be monospecific or multispecific (e.g., bispecific). Examples of binding molecules or fragments encompassed within the term "antibody" include, but are not limited to (i) a Fab' or Fab fragment, a monovalent fragment consisting of the $V_L$, $V_H$, $C_L$ and $C_H1$ domains, or a monovalent antibody as described in the international patent publication number WO2007059782; (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of a $V_L$ and $V_H$ domains, (v) a dAb fragment (see Ward et al., 1989, *Nature* 341, 544-546), which consists essentially of a $V_H$ domain and also called domain antibodies (see Holt et al, 2003, *Trends Biotechnol.* 21(11):484-90); (vi) camelid or nanobodies (see Revets et al., 2005, *Expert Opin Biol Ther.* 5(1):111-24) and (vii) an isolated complementarity determining region (CDR).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or during gene rearrangement or by somatic mutation in vivo). The term "mouse or murine monoclonal antibody" refers to antibodies displaying a single binding specificity which have variable and constant regions derived from murine or mouse germline immunoglobulin sequences.

The term "fusion protein" as used herein includes Fc fusion protein and receptor-Fc fusion protein. A fusion protein may be any polypeptide formed by expression of a chimeric gene made by combining more than one DNA sequence of different origins, typically by cloning one gene into an expression vector in frame with a second gene such that the two genes are encoding one continuous polypeptide.

In one aspect, the invention provides a method described herein for producing a recombinant polypeptide or protein of interest. In some embodiments, the recombinant polypeptide or protein of interest is selected from the group consisting of an antibody, antigen-binding protein, fusion protein, Fc fusion protein, and receptor-Fc fusion protein.

Cell Expression Systems

The use of cell expression systems is a prerequisite for high production of such polypeptides or proteins in cell culture.

A product according to the invention is a polypeptide, or a protein, which is expressed in the cells and is harvested from the cultivation system, i.e. the cells and/or the cell medium. It can be any polypeptide or protein of interest (supra).

Expression vectors typically use strong gene promoters to drive product mRNA transcription. In a further aspect, the invention relates to an expression vector encoding a polypeptide, e.g., an antibody, antigen-binding protein or fusion protein, of interest. Such expression vectors may be used in the methods of the invention for recombinant production of polypeptides or proteins of interest via cell culture.

An expression vector in the context of the methods of the invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. Such nucleic acid vectors and the usage thereof are well known in the art. See, for instance, U.S. Pat. Nos. 5,589,466 and 5,973,972.

A vector comprising a nucleic acid molecule encoding the polypeptide or protein of interest is provided in the host cell, wherein the nucleic acid molecule is operatively linked to an expression control sequence suitable for expression in a mammalian host cell.

Expression control sequences are engineered to control and drive the transcription of polypeptide-encoding genes of interest, and subsequent expression of polypeptides or proteins in various cell systems. Plasmids combine an expressible gene of interest with expression control sequences (i.e., expression cassettes) that comprise desirable elements such as, for example, promoters, enhancers, selectable markers, operators, etc. In an expression vector nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to control transcription of nucleotide sequence. The expression of a nucleotide sequence may be placed under control of any promoter or enhancer element known in the art. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters).

In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules encoding the polypeptide or protein of interest may also be operatively linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable.

Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene). Selectable (or selection) markers are typically utilized within stable cell line development.

In certain embodiments, the vector comprises one or more selectable marker genes selected from the group consisting of bla, bls, BSD, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), yellow fluorescent protein (YFP), or the like.

For the purposes of this invention, gene expression in eukaryotic cells may be tightly regulated using a strong promoter that is controlled by an operator that is in turn regulated by a regulatory fusion protein (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene of interest in such a way that the gene may be regulated by the binding of the RFP to the operator and, as a result, prevents or allows transcription of the gene of interest. A number of operators in prokaryotic cells and bacteriophage have been well characterized. See Neidhardt, ed. *Escherichia coli* and *Salmonella*; Cellular and Molecular Biology 2d. Vol 2 ASM Press, Washington D.C. 1996. These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda $P_R$ and the phage P22 ant/mnt genes which bind the repressor proteins encoded by lambda cI and P22 arc. In some embodiments, when the transcription blocking domain of the RFP is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box.

In certain embodiments, the operator is selected from the group consisting of tet operator (tetO), NotI recognition sequence, LexA operator, lactose operator, tryptophan operator and Arc operator (AO). In some embodiments, the repressor protein is selected from the group consisting of TetR, LexA, LacI, TrpR, Arc, LambdaC1 and GAL4. In other embodiments, the transcription blocking domain is derived from a eukaryotic repressor protein, e.g., a repressor domain derived from GAL4.

In an exemplary cell expression system, cells are engineered to express the tetracycline repressor protein (TetR) and a polypeptide of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription and thus translation (expression) of the polypeptide of interest occurs. See, e.g., U.S. Pat. No. 7,435,553, which is herein incorporated by reference in its entirety.

Such cell expression systems may be used to "turn on" production of the polypeptide of interest during production culture only. Thus, antibiotics, such a tetracycline or other suitable inducers, may be added to the bioreactor to a first cell culture.

Another exemplary cell expression system includes regulatory fusion proteins such as TetR-$ER_{LBD}$T2 fusion protein, in which the transcription blocking domain of the fusion protein is TetR and the ligand-binding domain is the estrogen receptor ligand-binding domain ($ER_{LBD}$) with T2 mutations ($ER_{LBD}$T2; Feil et al., 1997, *Biochem. Biophys. Res. Commun.* 237:752-757). When tetO sequences were placed downstream and proximal to the strong CMV-MIE promoter, transcription of the nucleotide sequence of interest from the CMV-MIE/tetO promoter was blocked in the presence of tamoxifen and unblocked by removal of tamoxifen. In another example, use of the fusion protein Arc2-$ER_{LBD}$T2, a fusion protein consisting of a single chain dimer consisting of two Arc proteins connected by a 15 amino acid linker and the $ER_{LBD}$T2 (supra), involves an Arc operator (AO), more specifically two tandem arc operators immediately downstream of the CMV-MIE promoter/enhancer. Cell lines may be regulated by Arc2-$ER_{LBD}$T2, wherein cells expressing the protein of interest are driven by a CMV-MIE/ArcO2 promoter and are inducible with the removal of tamoxifen. See, e.g., US 20090162901A1, which is herein incorporated by reference. In some embodiments, the vector comprises a CMV-MIE/TetO or CMV-MIE/AO2 hybrid promoter.

Suitable vectors used in the methods of the invention may also employ Cre-lox tools for recombination technology in order to facilitate the replication of a gene of interest. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. See, e.g., Araki et al., 1995, *PNAS* 92:160-4; Nagy, A. et al., 2000, *Genesis* 26:99-109; Araki et al., 2002, *Nuc Acids Res* 30(19):e103; and US20100291626A1, all of which are herein incorporated by reference. In another recombination strategy, yeast-derived FLP recombinase may be utilized with the consensus sequence FRT. See also, Dymecki, S., 1996, *PNAS* 93(12): 6191-6196.

In another aspect, a gene (i.e., a nucleotide sequence encoding a recombinant polypeptide of interest) is inserted within an expression-enhancing sequence of the expression cassette, and is optionally operably linked to a promoter, wherein the promoter-linked gene is flanked 5' by a first recombinase recognition site and 3' by a second recombinase recognition site. Such recombinase recognition sites allow Cre-mediated recombination in the host cell of the expression system. In some instances, a second promoter-linked gene is downstream (3') of the first gene and is flanked 3' by the second recombinase recognition site. In still other instances, a second promoter-linked gene is flanked 5' by the second recombinase recognition site, and flanked 3' by a third recombinase recognition site. In some embodiments, the recombinase recognition sites are selected from a loxP site, a lox511 site, a lox2272 site, and a FRT site. In other embodiments, the recombinase recognition sites are different. In a further embodiment, the host cell comprises a gene capable of expressing a Cre recombinase.

In one embodiment, the vector comprises a first gene encoding a light chain of an antibody or a heavy chain of an antibody of interest, and a second gene encoding a light chain of an antibody or a heavy chain of an antibody of interest.

It is understood that one or more vectors carrying one or more nucleic acid sequences encoding for and expressing the protein of interest may be employed in such an expression system.

Cells of the invention may also be engineered to increase product expression via coexpression of proteins such as chaperones, apoptosis inhibitors, protein degradation inhibitors, or other protein which may enhance the expression or stability of the product.

In some embodiments, the vector further comprises an X-box-binding-protein 1 (mXBP1) and/or an EDEM2 gene capable of enhancing protein production/protein secretion through control of the expression of genes involved in protein folding in the endoplasmic reticulum (ER). See, e.g., Ron D, and Walter P., 2007, *Nat Rev Mol Cell Biol.* 8:519-529; Olivari et al., 2005, *J. Biol. Chem.* 280(4): 2424-2428, Vembar and Brodsky, *Nat. Rev. Mol. Cell. Biol.* 9(12): 944-957, 2008.

The use of transiently transfected cells which produce rapidly significant quantities of the product may also be carried out for the optimization of a cell culture process, however stable transfection is typically utilized for production scales of large volume.

In the context of the present invention, the metabolically shifted cell may contain any or all of the elements of a cell expression system as described herein necessary for the efficient recombinant production of a protein of interest.

In an even further aspect, the invention relates to a metabolically shifted recombinant eukaryotic host cell which produces a protein of interest. Examples of host cells include mammalian cells, such as CHO, PER.C6, murine lymphoid, and murine hybridoma cell lines (supra). For example, in one embodiment, the present invention provides a metabolically shifted cell comprising a nucleic acid sequence stably integrated into the cellular genome that comprises a sequence encoding for a protein of interest. In another embodiment, the present invention provides a metabolically shifted cell comprising a non-integrated (i.e., episomal) nucleic acid sequence, such as a plasmid, cosmid, phagemid, or linear expression element, which comprises a sequence encoding for a protein of interest.

"Harvesting" or "cell harvesting" takes place at the end of a production batch in an upstream process. Cells are separated from medium by a number of methods such as filtration, cell encapsulation, cell adherence to microcarriers, cell sedimentation or centrifugation. Purification of protein takes place in additional steps to isolate the protein product. Polypeptides or proteins may be harvested from either the cells or cell culture media.

Protein purification strategies are well-known in the art. Soluble forms of the polypeptide, such as antibodies, antibody-binding fragments and Fc-containing proteins, may be subjected to commercially available concentration filters, and subsequently affinity purified by well-known methods, such as affinity resins, ion exchange resins, chromatography columns, and the like. Membrane-bound forms of the polypeptide can be purified by preparing a total membrane fraction from the expressing cell and extracting the membranes with a nonionic detergent such as TRITON® X-100 (EMD Biosciences, San Diego, Calif., USA). Cytosolic or nuclear proteins may be prepared by lysing the host cells (via mechanical force, sonication, detergent, etc.), removing the cell membrane fraction by centrifugation, and retaining the supernatant.

In a further aspect, the invention relates to a method for producing an antibody, or antigen-binding protein, or fusion protein of interest, said method comprising the steps of a) culturing cells according to the method as described herein above, b) harvesting the cells, and c) purifying the polypeptide or protein, such as antibody, or antigen-binding protein, or fusion protein, from the cells or cell culture media.

The following examples are provided to describe to those of ordinary skill in the art how to make and use methods and compositions of the invention, and are not intended to limit the scope of what the inventors regard as their invention. Efforts have been made to ensure the accuracy with respect to numbers used (e.g., amounts, concentrations, temperature, etc.) but some experimental errors and deviations should be accounted for.

EXAMPLES

Example 1

Determining Metabolic Shift Parameters: Fusion Protein-Producing Cell Line

CHO cells were transfected with DNA expressing a fusion protein. The fusion protein-producing CHO cell line was incubated in a seed vessel culture, in proprietary media containing soy, and parameters such as online pH, offline lactate and viable cell count, were measured and recorded to determine metabolic state (#1, #2, or #3 of FIG. 1A). Base usage was also monitored and normalized to 1 for this cell line (FIG. 1A).

Cells under condition #1 and condition #2 were used to inoculate replicate production bioreactors when the pH was controlling at the bottom end of the control range and lactate and VCC were increasing. Cells under condition #3 were inoculated when the pH was starting to increase off the bottom of the control range, i.e., base usage had stopped, indicating lactate remetabolization (i.e., consumption). Cell growth in condition #3 had entered post-exponential growth phase. All production bioreactors were run with the same operating conditions.

Product titer (FIG. 1B) and lactate profiles (FIG. 1C) were measured in each production bioreactor using known methods to determine the impact of seed train metabolic state #1, #2 or #3. Production bioreactor trendlines represent the average of duplicate bioreactors with error bars that represent ± one standard deviation.

Figure 1B:
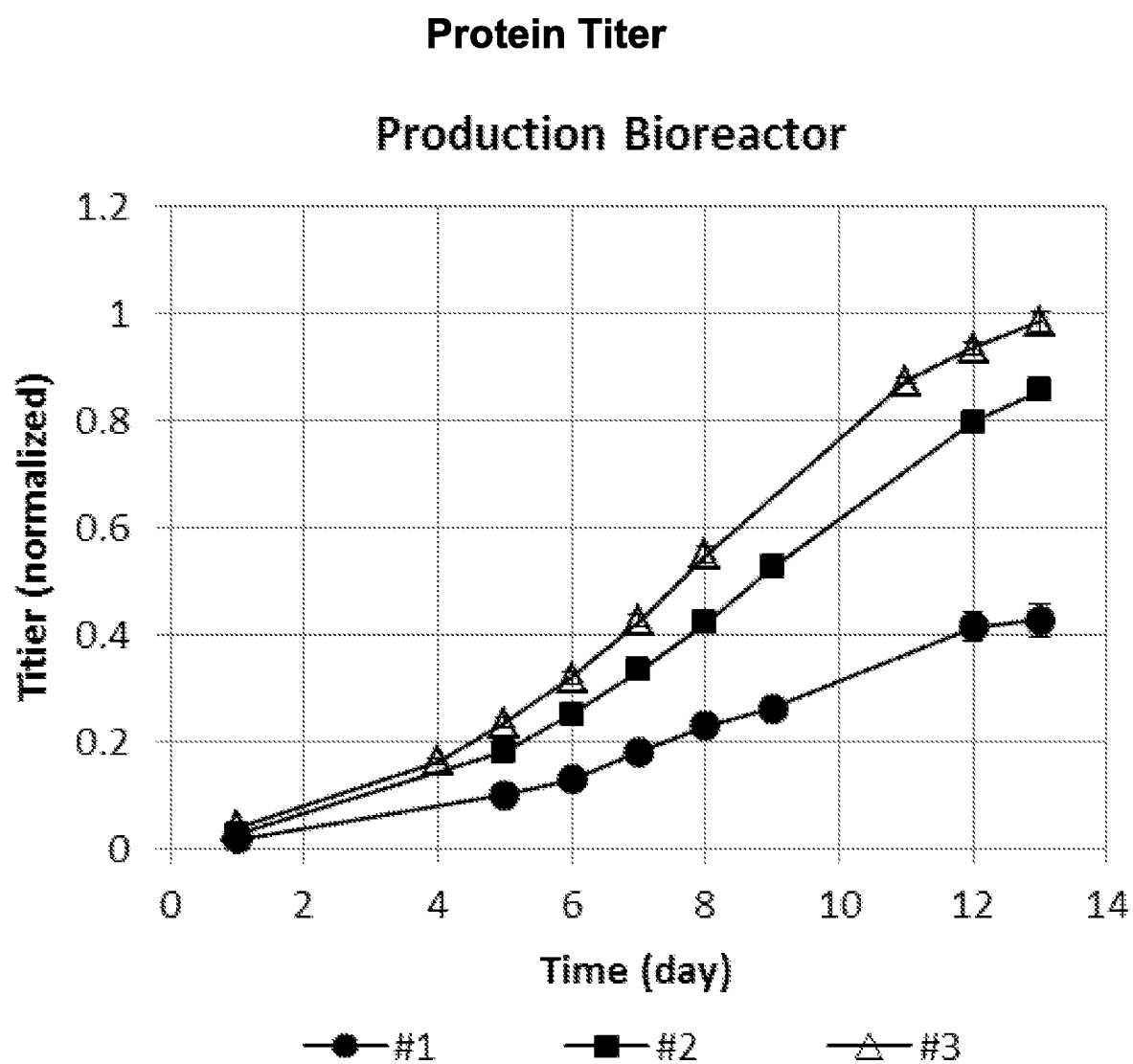
Figure 1C:
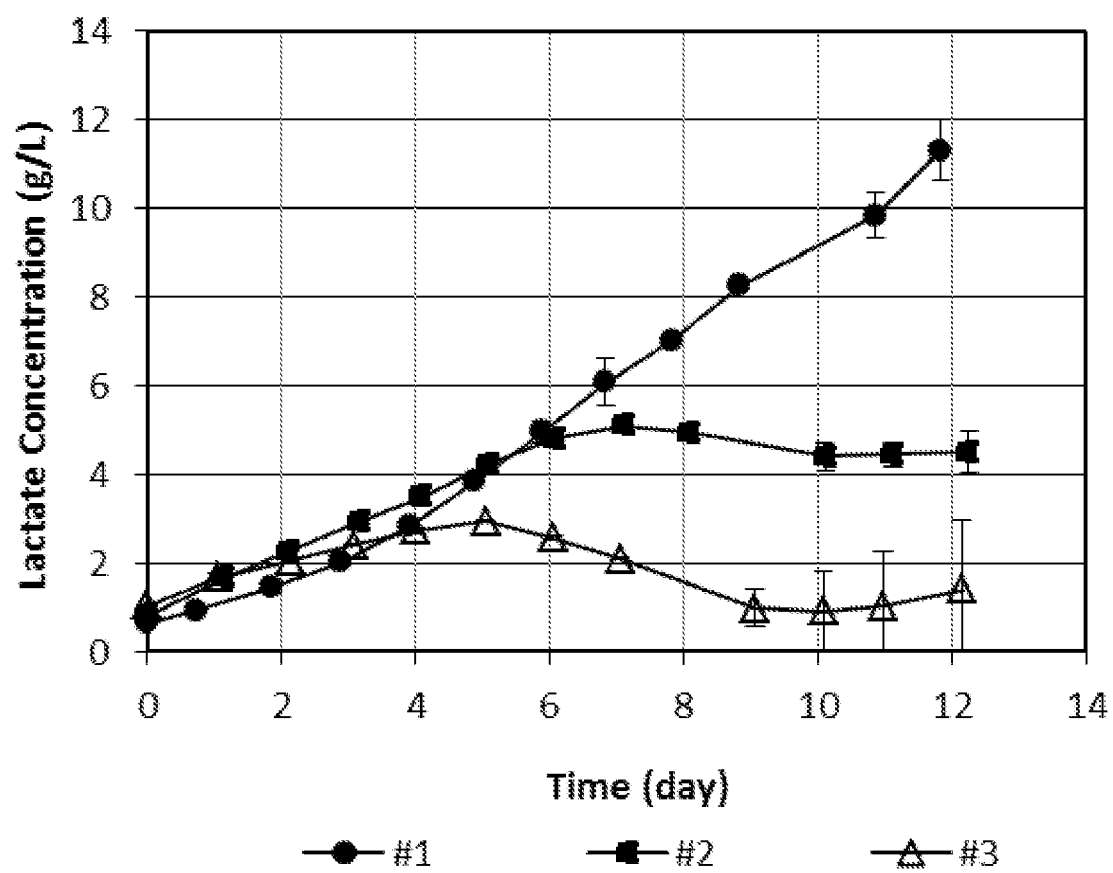

Condition #3 cells had the most significant effect on the productivity and lactate accumulation in the second cell culture, resulting in a greater than 2-fold increase in product titer (compared to Conditions #1 and #2), in the production bioreactor (FIG. 1B). Condition #3 cells also resulted in decreased lactate concentration following transfer to the second cell culture (compared to Conditions #1 and #2—FIG. 1C). Condition #3 cells have a lactate profile indicative of net lactate consumption (FIG. 1C at 8-12 days of cell culture). Cells transferred from the first culture under Condition #1 (i.e., prior to a metabolic shift in first culture) do not achieve net lactate consumption in the production bioreactor.

Example 2

Determining Metabolic Shift Parameters, Antibody-Producing Cell Line

Figure 2A:
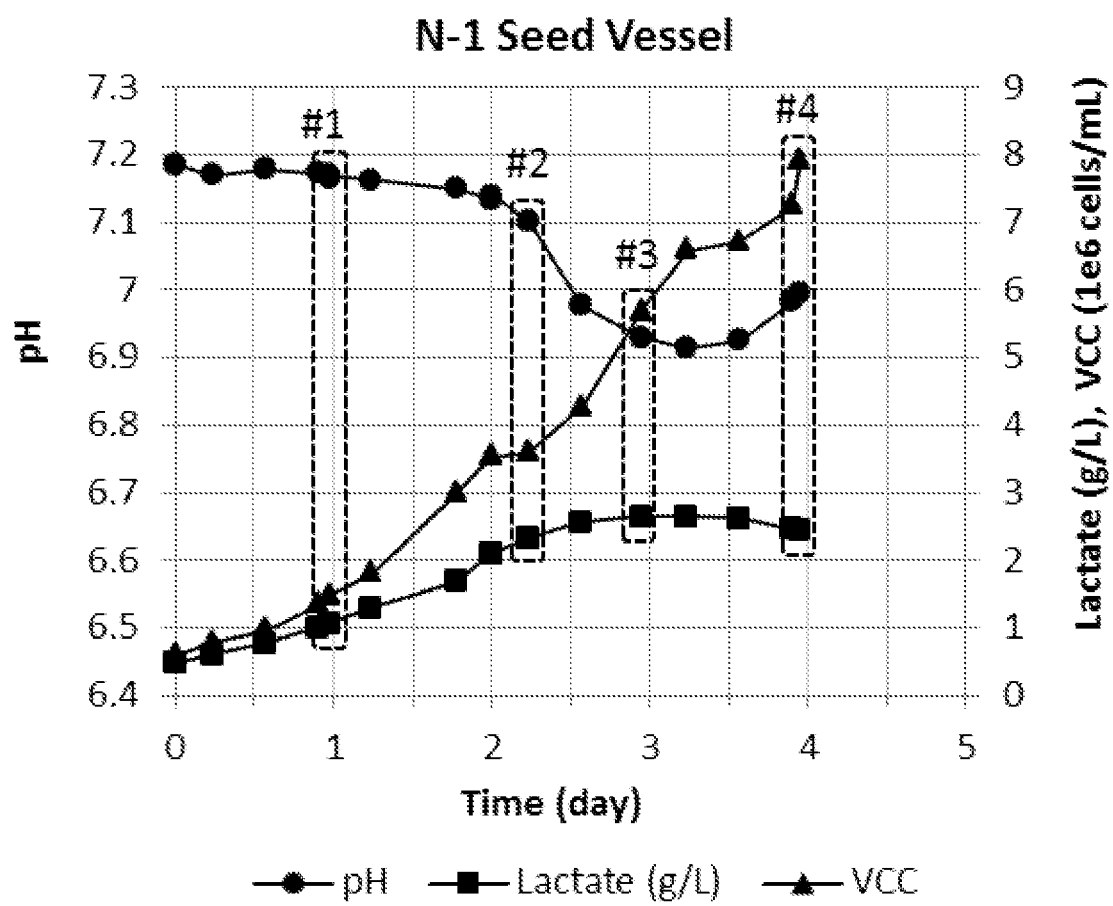
FIGS. 2A-2C: An antibody-producing CHO cell line seed vessel was used to inoculate replicate production bioreactors in a chemically defined process at four different metabolic states (offline pH and lactate) and viable cell counts (FIG. 2A). The parameters (i.e., time, pH, lactate, and VCC) for each cell culture (Condition #1, #2, #3 and #4) for which cells were transferred to production bioreactors is indicated by open rectangles (dotted lines). All production bioreactors were run with the same operating conditions. Condition #1 was lost after one week. The impact of each seed train and its metabolic state on a production bioreactor protein titer (FIG. 2B) and lactate accumulation (FIG. 2C) is also shown. Production bioreactor trendlines represent the average of duplicate bioreactors with error bars that represent ± one standard deviation.

An antibody-producing CHO cell line seed vessel was used to inoculate replicate production bioreactors similar to Example 1, however in chemically defined medium. Four different metabolic states were measured (monitoring offline pH, lactate and viable cell counts—#1, #2, #3, and #4 of FIG. 2A). VCC continued to increase during the duration of the seed vessel incubation when production bioreactors were inoculated.

Condition #1 was inoculated very early in the seed train when the pH was still at the top end of the control range and when the lactate was low but increasing. Condition #2 was inoculated when the pH was starting to decrease and lactate was increasing and approaching peak levels. Condition #3 was inoculated when the pH was near the bottom of the control range and lactate levels had plateaued. Condition #4 was inoculated when the pH was starting to increase off the bottom of the control range and during lactate remetabolization (i.e., lactate consumption). All production bioreactors were run with the same operating conditions. Condition #1 was lost after one week.

Figure 2B:
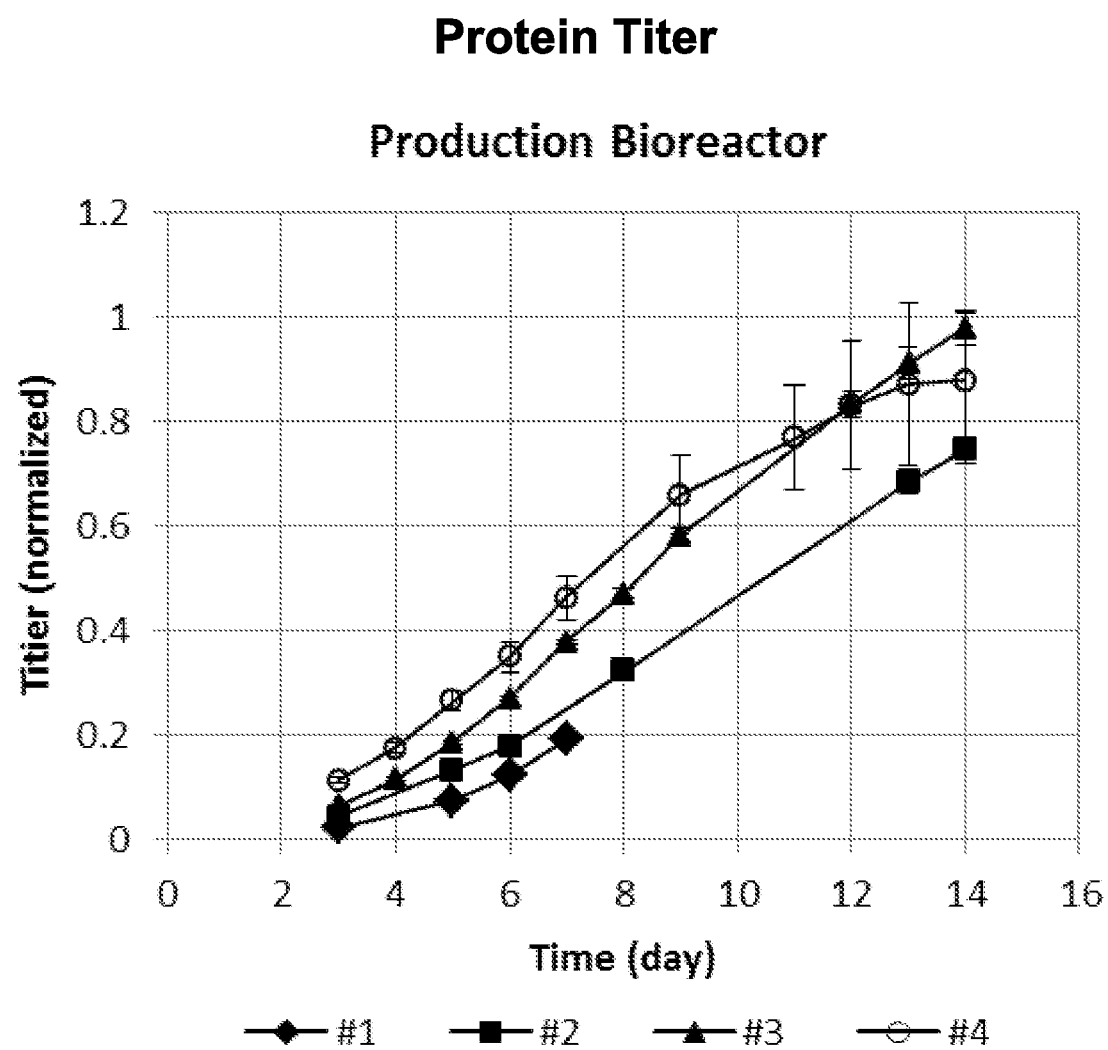
Figure 2C:
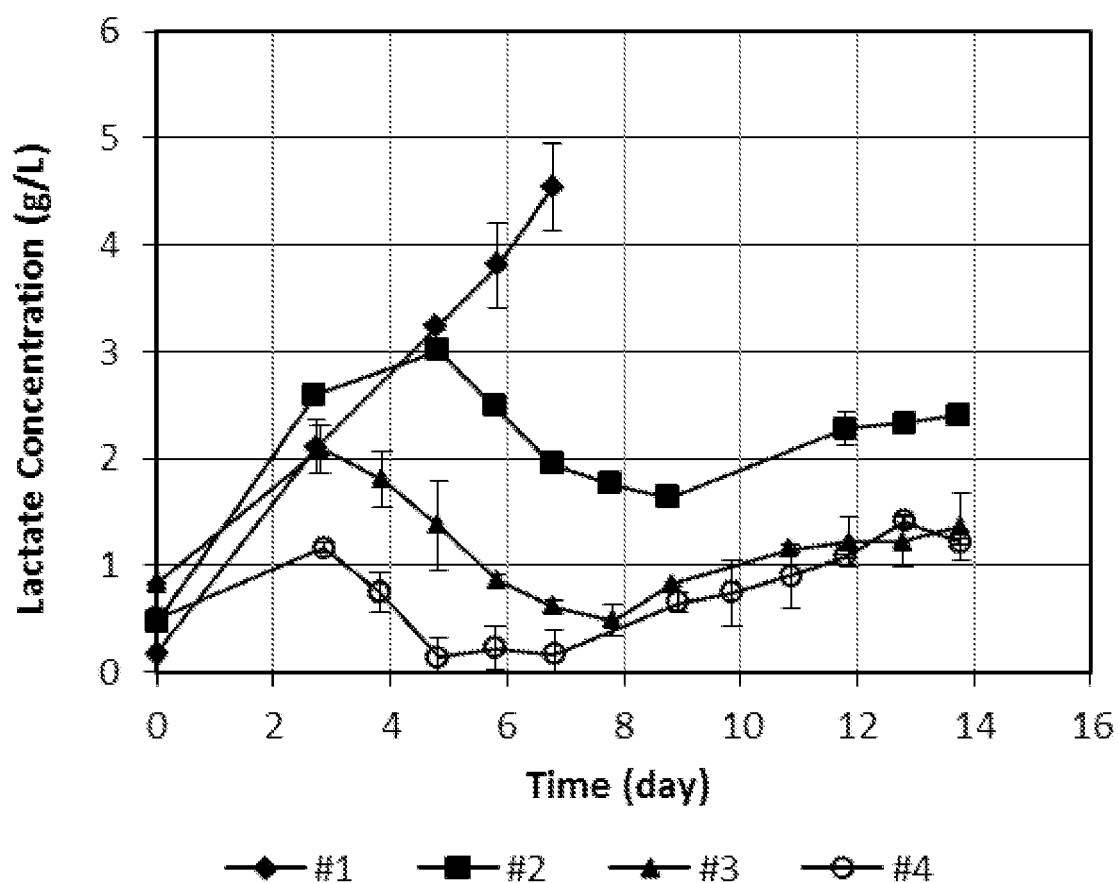

The impact of seed train metabolic state on production bioreactor titer (FIG. 2B) and lactate (FIG. 2C) profiles was determined. Production bioreactor trendlines represent the average of duplicate bioreactors with error bars that represent ± one standard deviation.

Condition #3 and #4 cells had the most significant effect on the productivity. Condition #3 and #4 cells also resulted in reduced lactate concentration in the production bioreactor (compared to Conditions #1 and #2), which is indicative of a metabolic phenotype for lactate consumption (see FIGS. 2B and 2C). Similar to Example 2, cells transferred from first culture under Condition #1 do not achieve net lactate consumption during the production phase. Conditions #2, #3 and #4 achieve net lactate consumption during the production phase, however Condition #4 is most optimal since net lactate consumption occurs earlier than the other conditions, and the peak lactate level is the lowest.

Example 3

Optimizing Bioreactor Titer Production by Modifying Final Viable Cell Concentration CHO cells were transfected with DNA expressing a protein of interest. The antibody-producing CHO cell line was incubated in a seed vessel culture, in proprietary media, and parameters such as lactate and viable cell concentration were measured and recorded to determine metabolic state of the cells in the N-2 and N-1 seed train cell cultures. As shown in FIG. 4, cells cultured in a first seed train culture (N-2) to a viable cell density of greater than $3.0\times10^6$ cells/mL, e.g., $4.5\times10^6$ cells/mL (diamond), resulted in a reduced rate of lactate accumulation throughout culture without affecting cell growth in either the first seed train culture (N-2) or the second seed train culture step (N-1). Lower peak lactate concentrations in a second seed train culture were achieved after cells in the first seed train culture (N-2) were grown to a VCC of greater than $3.0\times10^6$ cells/mL (diamond). Taken together, the foregoing experimental results show that culturing cells to a final VCC of greater than $3.0\times10^6$ cells/mL causes a shift in the metabolic profile of culture cells to lactate consumption.

Figure 5A:
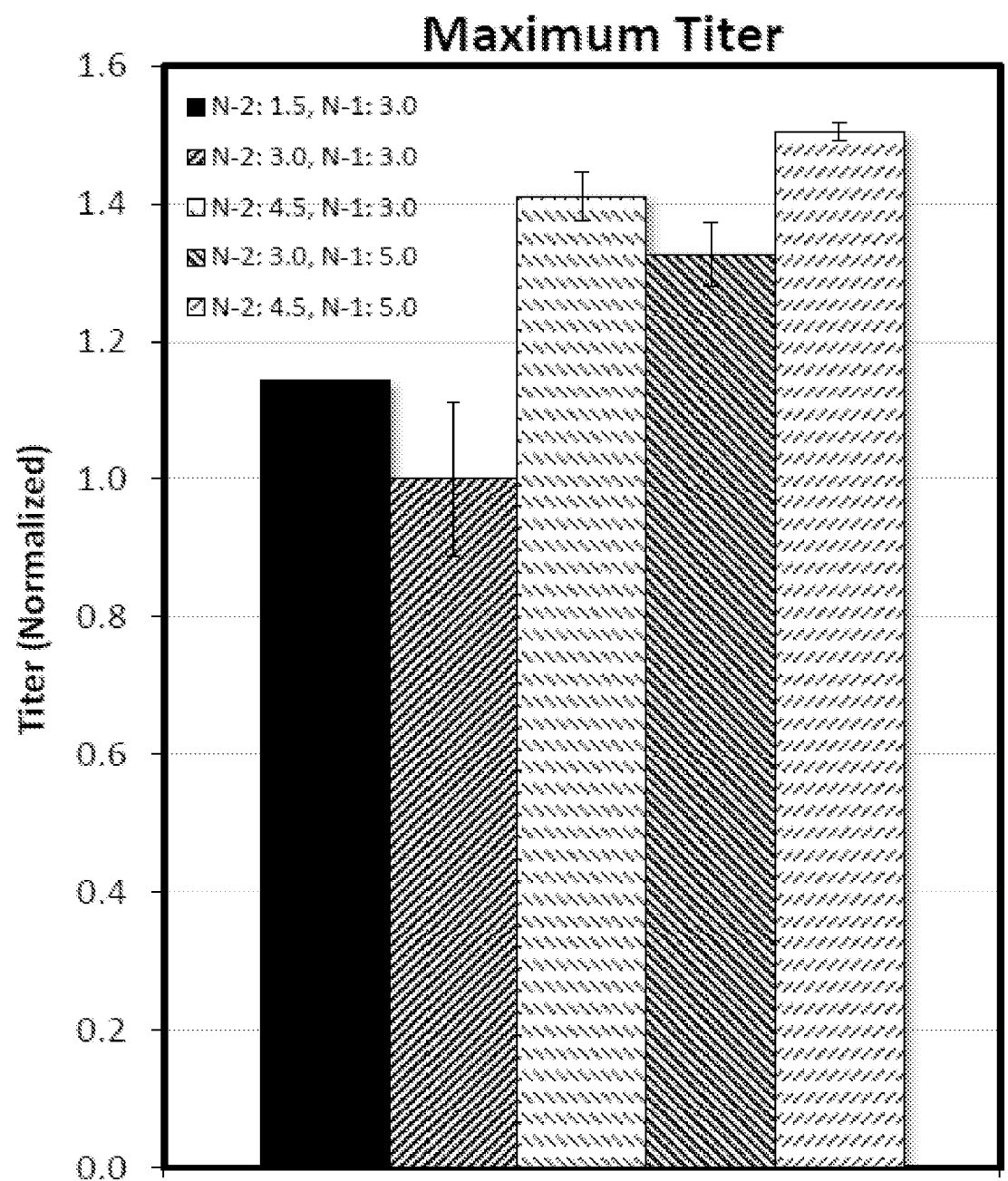
FIGS. 5A-5B: Maximum protein titer profiles of the production cell culture bioreactor.
Figure 5B:
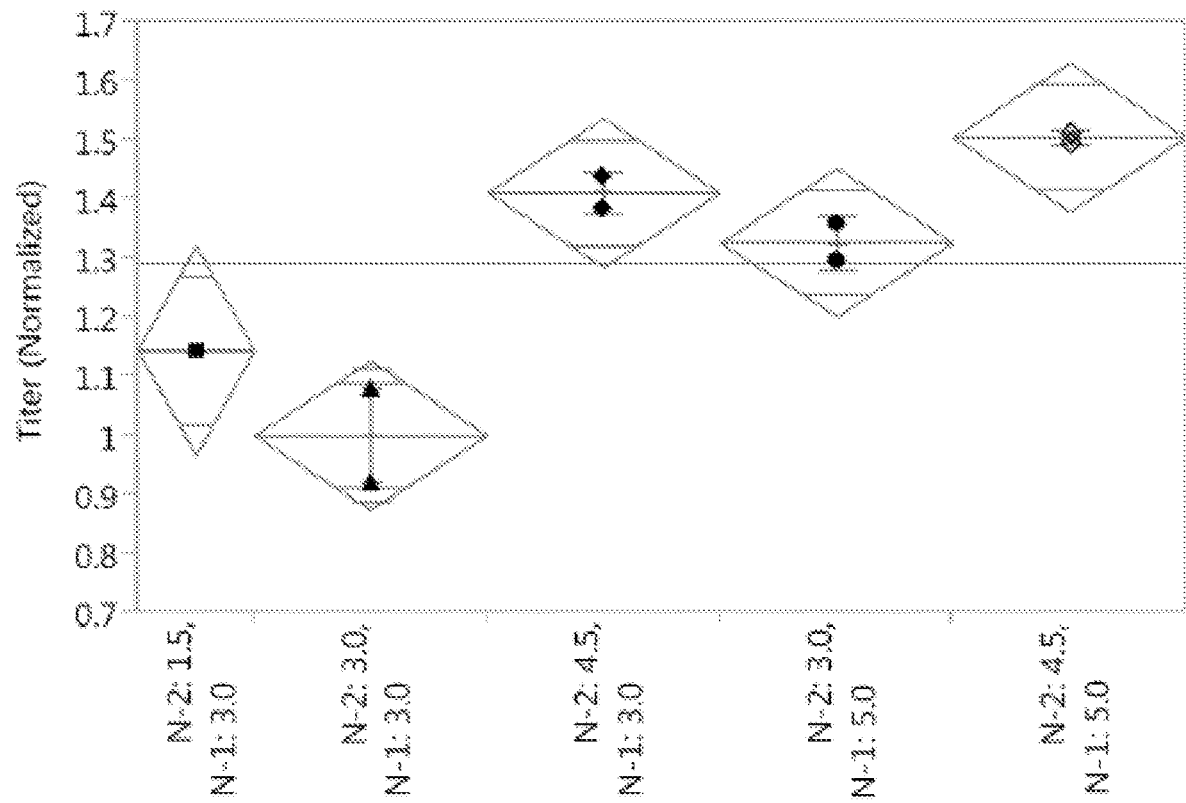
Figure 6:
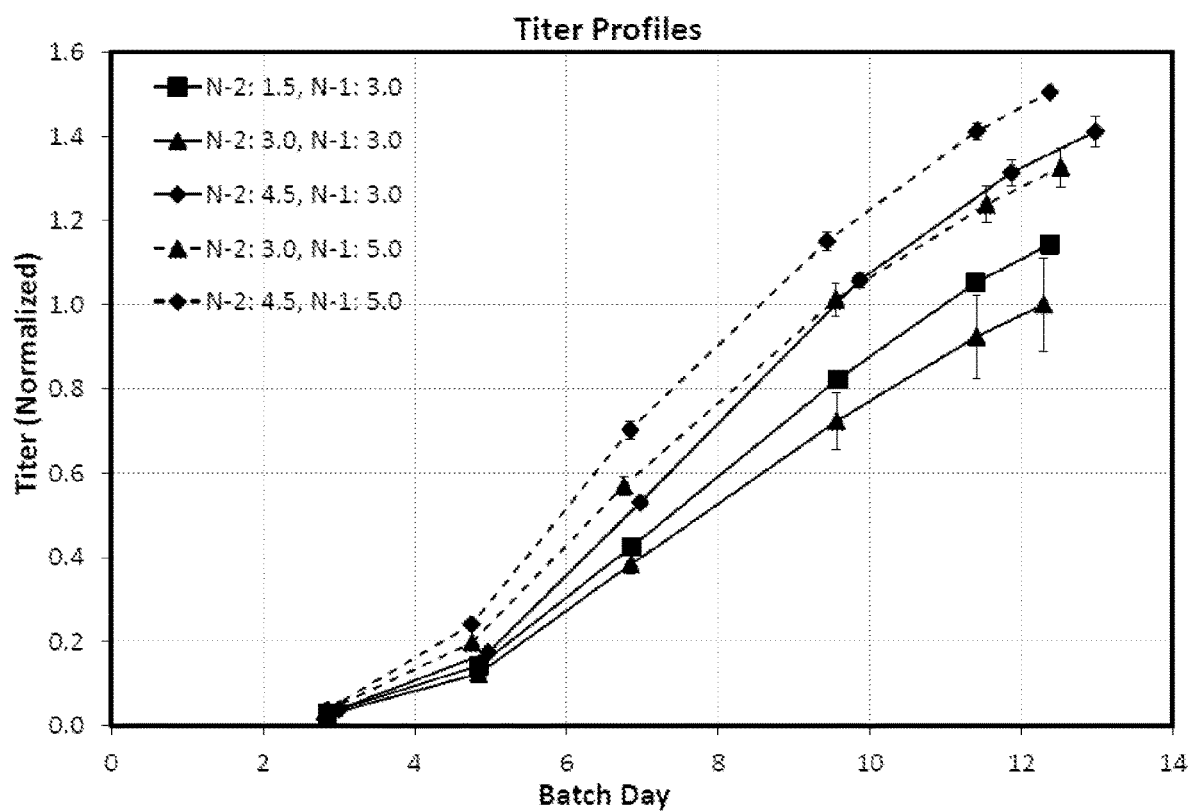
FIG. 6 shows that increasing the final viable cell culture density in the N-2 and/or N-1 seed train cell culture steps results in an increase in production culture protein titer output at all days of cell culture growth.

As shown in FIGS. 5A-B and 6, the resulting shift to lactate consumption increases maximum protein titer in a production cell culture bioreactor. Culturing cells to a viable cell concentration of greater than $3.0\times10^6$ cells/mL in a first seed train culture (N-2: $4.5\times10^6$ cells/mL, N-1: $3.0\times10^6$ cells/mL) alone resulted in a statistically significant increase in maximum protein titer when compared to titer profiles resulting from cells cultured to a lower viable cell concentration in the first seed train culture (N-2: $1.5\times10^6$ cells/mL, N-1: $3.0\times10^6$ cells/mL or N-2: $3.0\times10^6$ cells/mL, N-1: $3.0\times10^6$ cells/mL).

Additionally, culturing cells to a viable cell concentration of greater than $3.0\times10^6$ cells/mL in a second seed train culture (N-2: $3.0\times10^6$ cells/mL, N-1: $5.0\times10^6$ cells/mL) alone also resulted in a statistically significant increase in maximum protein titer when compared to titer profiles resulting from cells cultured to a lower viable cell concentration in the second seed train culture (N-2: $1.5\times10^6$ cells/mL, N-1: $3.0\times10^6$ cells/mL or N-2: $3.0\times10^6$ cells/mL, N-1: $3.0\times10^6$ cells/mL).

Increasing the final VCCs in both the N-2 and N-1 seed train culture steps to greater than $3.0\times10^6$ cells/mL (e.g., $4.5\times10^6$ cell/mL and $5\times10^6$ cells/mL) provides the greatest increase in maximum production protein titer, i.e., about a 1.5 fold increase in the maximum titer when compared to the maximum titer exhibited in the production culture step when the N-2 and N-1 seed train cell culture steps were each grown to a final VCC of $3.0\times10^6$.

As shown in FIG. 5B, growing the VCCs in both the N-2 and N-1 seed train culture steps to greater than $3.0\times10^6$ cells/mL (N-2: $4.5\times10^6$ cell/mL, N-1: $5\times10^6$ cells/mL) resulted in the greatest maximum protein titer when all conditions were compared. However, culturing cells in either the N-2 or N-1 seed train cultures alone to a final viable cell concentration of greater than $3.0\times10^6$ cells/mL (FIG. 5B, N-2: $4.5\times10^6$ cell/mL, N-1: $3\times10^6$ cells/mL and N-2: $3.0\times10^6$ cell/mL, N-1: $5\times10^6$ cells/mL) also provided a increase in maximum protein titer when compared to when cells in the N-2 and N-1 seed train cultures were grown to a final viable cell concentration of $3.0\times10^6$ cells/mL or lower (FIG. 5B, N-2: $1.5\times10^6$ cell/mL, N-1: $3.0\times10^6$ cells/mL and N-2: $3.0\times10^6$ cell/mL, N-1: $3.0\times10^6$ cells/mL). See, also FIG. 6.

Figure 7A:
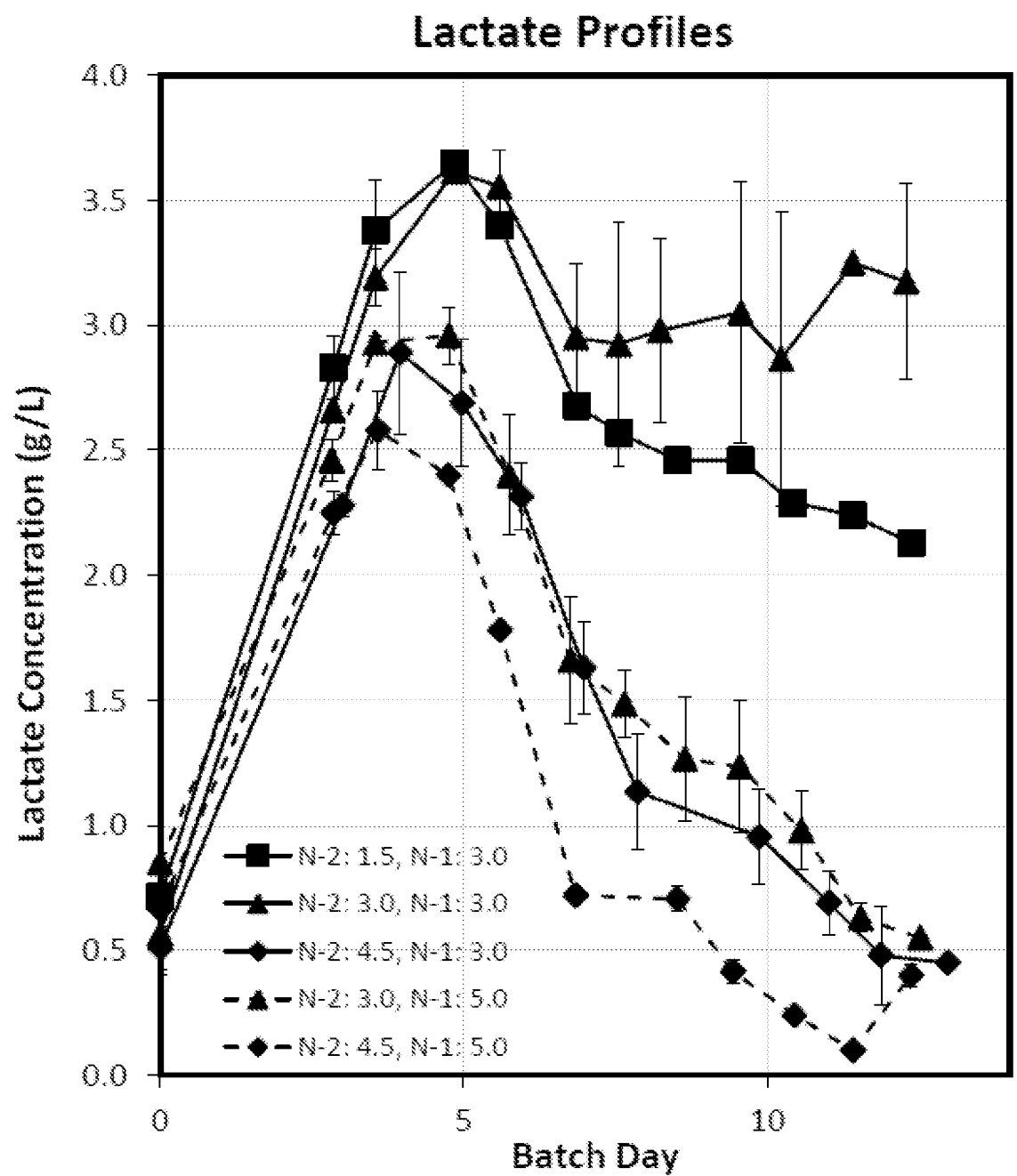
FIGS. 7A-7B show lactate profiles of the production cell culture bioreactor.
Figure 7B:
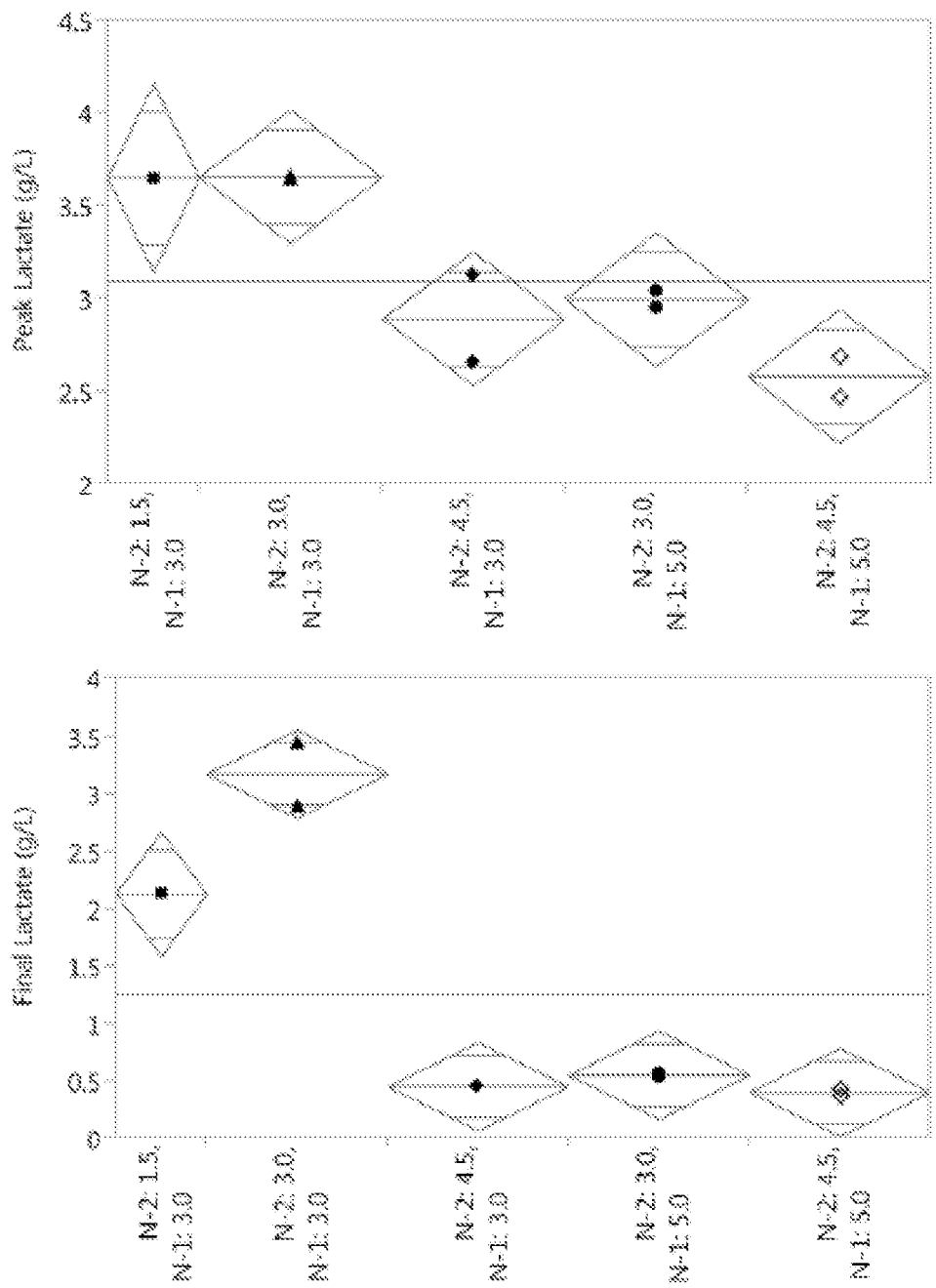

FIGS. 7A-B shows a comparison of the lactate profiles of the production cell culture bioreactor across all representative culture conditions. Specifically, an increase of the viable cell concentration in a first seed train culture (N-2) to a viable cell concentration of greater than $3.0\times10^6$ cells/mL (N-2: $4.5\times10^6$ cells/mL, N-1: $3.0\times10^6$ cells/mL) results in lower peak and final lactate concentration when compared to peak and final lactate profiles resulting from a lower viable cell concentration in the first seed train culture (e.g., N-2: $1.5\times10^6$ cells/mL, N-1: $3.0\times10^6$ cells/mL or N-2: $3.0\times10^6$ cells/mL, N-1: $3.0\times10^6$ cells/mL).

Similarly, culturing cells in a second seed train cell culture to a viable cell concentration of greater than $3.0\times10^6$ cells/mL alone (N-2: $3.0\times10^6$ cells/mL, N-1: $5.0\times10^6$ cells/mL) results in lower peak and final lactate concentration when compared to peak and final lactate profiles resulting from a lower viable cell concentration in the second seed train culture (e.g., N-2: $1.5\times10^6$ cells/mL, N-1: $3.0\times10^6$ cells/mL or N-2: $3.0\times10^6$ cells/mL, N-1: $3.0\times10^6$ cells/mL in FIG. 7B).

Increasing the final VCCs in both the N-2 and N-1 seed train culture steps to greater than $3.0\times10^6$ cells/mL (e.g., $4.5\times10^6$ cell/mL and $5\times10^6$ cells/mL) results the greatest reduction lactate accumulation rate in the production culture step when compared to when the N-2 and N-1 seed train cell cultures were each grown to a final VCC of $3.0\times10^6$ cells/mL or lower. Reduced peak lactate concentrations were also observed in the production cell culture bioreactor for any seed train culture process in which the final N-2 and/or N-1 viable cell concentration(s) was greater than $3.0\times10^6$ cells/mL (FIG. 7B, N-2: $4.5\times10^6$ cell/mL, N-1: $3.0\times10^6$ cells/mL; N-2: $3.0\times10^6$ cell/mL, N-1: $5\times10^6$ cells/mL; and N-2: $4.5\times10^6$ cell/mL, N-1: $5\times10^6$ cells/mL) when compared to final N-2 and/or N-1 viable cell concentration(s) below $3.0\times10^6$ cells/mL in the N-2 and N-1 seed train cultures (FIG. 7B, N-2: $1.5\times10^6$ cells/mL, N-1: $3.0\times10^6$ cells/mL or N-2: $3.0\times10^6$ cells/mL, N-1: $3.0\times10^6$ cells/mL).

Taken together, the foregoing experimental results clearly show that by increasing the final VCCs of either of the N-2 and N-1 bioreactors, independently as well as in combination, lower peak and final lactate concentrations are achieved in the production bioreactor.

What is claimed:

1. A method for culturing cells comprising:
   (a) culturing cells in a first cell culture to a viable cell concentration of $3.1\times10^6$ cells/mL to $5.0\times10^6$ cells/mL whereby a metabolic shift to lactate consumption has occurred, wherein the first cell culture is a seed train cell culture, wherein lactate accumulates in the first cell culture, and wherein said lactate in the first cell culture consists of lactate produced by the cells in the first cell culture;

(b) transferring an amount of cells from the first cell culture to a second cell culture, wherein the second cell culture is another seed train cell culture in another culture vessel, and wherein the second cell culture exhibits a reduced rate of lactate accumulation compared to that in an otherwise identical cell culture under otherwise identical conditions except transfer of cells from the first cell culture to the second cell culture is performed prior to the viable cell count reaching $3.0 \times 10^6$ cells/mL;

(c) culturing the transferred cells in the second cell culture; and (d) transferring an amount of cells from the second cell culture to a production bioreactor after the cells in the second cell culture have reached a viable cell concentration of $3.0 \times 10^6$ cells/mL to $5.0 \times 10^6$ cells/mL.

2. The method of claim 1, wherein the cells in the first cell culture are cultured to a viable cell concentration of $3.5 \times 10^6$ cells/mL to $5.0 \times 10^6$ cells/mL.

3. The method of claim 2, wherein the cells in the first cell culture are cultured to a viable cell concentration of $4.0 \times 10^6$ cells/mL, $4.5 \times 10^6$ cells/mL or $5.0 \times 10^6$ cells/mL.

4. The method of claim 1, wherein the cells in the first cell culture are cultured to a viable cell concentration of $4.5 \times 10^6$ cells/mL to $5.0 \times 10^6$ cells/mL.

5. The method of claim 1, wherein said viable cell concentration of the second cell culture is $3.5 \times 10^6$ cells/mL to $5.0 \times 10^6$ cells/mL.

6. The method of claim 5, wherein said viable cell concentration of the second cell culture is $3.5 \times 10^6$ cells/mL, $4.0 \times 10^6$ cells/mL, $4.5 \times 10^6$ cells/mL or $5.0 \times 10^6$ cells/mL.

7. The method of claim 1, wherein said viable cell concentration of the second cell culture is $4.0 \times 10^6$ cells/mL to $5.0 \times 10^6$ cells/mL.

8. The method of claim 1, further comprising detecting a reduced rate of lactate accumulation in the second cell culture prior to transfer to the production bioreactor compared to that determined in an otherwise identical cell culture under otherwise identical conditions except transferring cells to the second cell culture is performed prior to the viable cell count reaching $3.0 \times 10^6$ cells/mL.

9. The method of claim 1, further comprising detecting said metabolic shift to lactate consumption by measuring the pH, lactate or base in the first cell culture prior to step (b).

10. The method of claim 9, wherein said metabolic shift to lactate consumption is detected based on an increase in the pH of the first cell culture medium without addition of base.

11. The method of claim 9, wherein said metabolic shift is detected based on measuring the lactate levels in the first cell culture.

12. The method of claim 1, wherein the metabolic shift occurs when the cells emerge from log growth phase or have reached stationary phase in the first cell culture.

13. The method of claim 1, wherein the cells in the first cell culture are transfected with DNA encoding a polypeptide of interest prior to culturing cells in the first cell culture.

14. The method of claim 13, further comprising maintaining the second cell culture and the cell culture in the production bioreactor under conditions that allow expression of said polypeptide of interest, and harvesting said polypeptide of interest from the cell culture in the production bioreactor.

15. The method of claim 14, wherein said protein of interest is selected from the group consisting of antibody, antigen-binding protein, and fusion protein.

* * * * *